(12) United States Patent
Quintanar

(10) Patent No.: US 11,975,134 B2
(45) Date of Patent: May 7, 2024

(54) BLOCKAGE AND LEAK DETECTION IN MULTIPLE DRESSING REDUCED PRESSURE WOUND THERAPY SYSTEMS

(71) Applicant: T.J.Smith and Nephew, Limited, Hull (GB)

(72) Inventor: Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 738 days.

(21) Appl. No.: 17/270,398

(22) PCT Filed: Aug. 21, 2019

(86) PCT No.: PCT/EP2019/072365
§ 371 (c)(1),
(2) Date: Feb. 22, 2021

(87) PCT Pub. No.: WO2020/043567
PCT Pub. Date: Mar. 5, 2020

(65) Prior Publication Data
US 2021/0187175 A1    Jun. 24, 2021

(30) Foreign Application Priority Data
Aug. 31, 2018  (GB) ..................... 1814158

(51) Int. Cl.
*A61M 1/00*   (2006.01)
(52) U.S. Cl.
CPC .............. *A61M 1/73* (2021.05); *A61M 1/915* (2021.05); *A61M 1/92* (2021.05); *A61M 1/96* (2021.05);
(Continued)

(58) Field of Classification Search
CPC .......... A61M 1/73; A61M 1/74; A61M 1/913; A61M 1/915; A61M 1/918; A61M 1/92;
(Continued)

(56) References Cited

U.S. PATENT DOCUMENTS 7,945,302 B2   5/2011  McAdams
8,682,442 B2   3/2014  McAdams
(Continued)

FOREIGN PATENT DOCUMENTS

WO   WO-2011135286 A1   11/2011
WO   WO-2012021553 A1   2/2012
(Continued)

OTHER PUBLICATIONS

International Search Report and Written Opinion for Application No. PCT/EP2019/072365, mailed on Nov. 12, 2019, 13 pages.
(Continued)

*Primary Examiner* — Benjamin J Klein
(74) *Attorney, Agent, or Firm* — Knobbe, Martens, Olson & Bear, LLP

(57) ABSTRACT

Embodiments of apparatuses and methods for providing negative pressure wound therapy to multiple wounds are disclosed. In some embodiments, presence of blockage in one or more fluid flow paths connecting a negative pressure source to one or more dressings can be performed. Determination of a blockage can be performed based on comparing one or more pressure measurements to at least one threshold. The at least one threshold can be determined based on detected capacities of the one or more dressings.

20 Claims, 17 Drawing Sheets

(52) U.S. Cl.
CPC ............... *A61M 1/985* (2021.05); *A61M 1/74* (2021.05); *A61M 1/982* (2021.05); *A61M 2205/15* (2013.01); *A61M 2205/18* (2013.01); *A61M 2205/3331* (2013.01); *A61M 2205/3382* (2013.01)

(58) Field of Classification Search
CPC ........ A61M 1/96; A61M 1/982; A61M 1/985; A61M 2205/15; A61M 2205/18; A61M 2205/3331; A61M 2205/3382; A61M 2205/3389; A61M 2205/75
See application file for complete search history.

(56) References Cited

U.S. PATENT DOCUMENTS

| | | |
|---|---|---|
| 8,974,429 B2 | 3/2015 | Gordon et al. |
| 9,526,439 B2 | 12/2016 | Connelly et al. |
| 9,737,649 B2 | 8/2017 | Begin et al. |
| 10,155,070 B2 | 12/2018 | Childress et al. |
| 10,744,239 B2 | 8/2020 | Armstrong et al. |
| 2010/0268111 A1 | 10/2010 | Drinan et al. |
| 2012/0123358 A1 | 5/2012 | Hall et al. |
| 2012/0190956 A1 | 7/2012 | Connolly |
| 2012/0209226 A1 | 8/2012 | Simmons et al. |
| 2015/0032031 A1* | 1/2015 | Hartwell ............... A61B 5/1073 600/587 |
| 2016/0045377 A1 | 2/2016 | Robinson et al. |
| 2016/0081580 A1 | 3/2016 | Bergelin et al. |
| 2016/0101282 A1 | 4/2016 | Bergelin et al. |
| 2016/0120706 A1 | 5/2016 | Collinson et al. |
| 2016/0184496 A1* | 6/2016 | Jaecklein ............... A61M 1/982 604/318 |
| 2017/0028111 A1 | 2/2017 | Tumey et al. |
| 2017/0156658 A1 | 6/2017 | Maharbiz et al. |
| 2017/0216501 A1* | 8/2017 | Armstrong ............ A61M 1/732 |
| 2017/0368239 A1* | 12/2017 | Askem .................. A61M 1/982 |
| 2018/0055359 A1 | 3/2018 | Shamim et al. |
| 2018/0168916 A1 | 6/2018 | Kelch et al. |
| 2019/0046697 A1 | 2/2019 | Locke et al. |
| 2019/0290499 A1 | 9/2019 | Askem et al. |
| 2020/0061253 A1 | 2/2020 | Long et al. |
| 2020/0338242 A1* | 10/2020 | Pratt ........................ A61M 1/96 |

FOREIGN PATENT DOCUMENTS

| | | |
|---|---|---|
| WO | WO-2015168720 A1 | 11/2015 |
| WO | WO-2016109041 A1 | 7/2016 |
| WO | WO-2017197357 A1 | 11/2017 |
| WO | WO-2018041854 A1 | 3/2018 |
| WO | WO-2018167199 A1 | 9/2018 |
| WO | WO-2018158250 A4 | 11/2018 |
| WO | WO-2018212849 A1 | 11/2018 |
| WO | WO-2019020551 A1 | 1/2019 |

OTHER PUBLICATIONS

Kci, "V.A.C. Therapy Clinical guidelines: a reference source for clinicians," Nov. 2005, 24 pages.

* cited by examiner

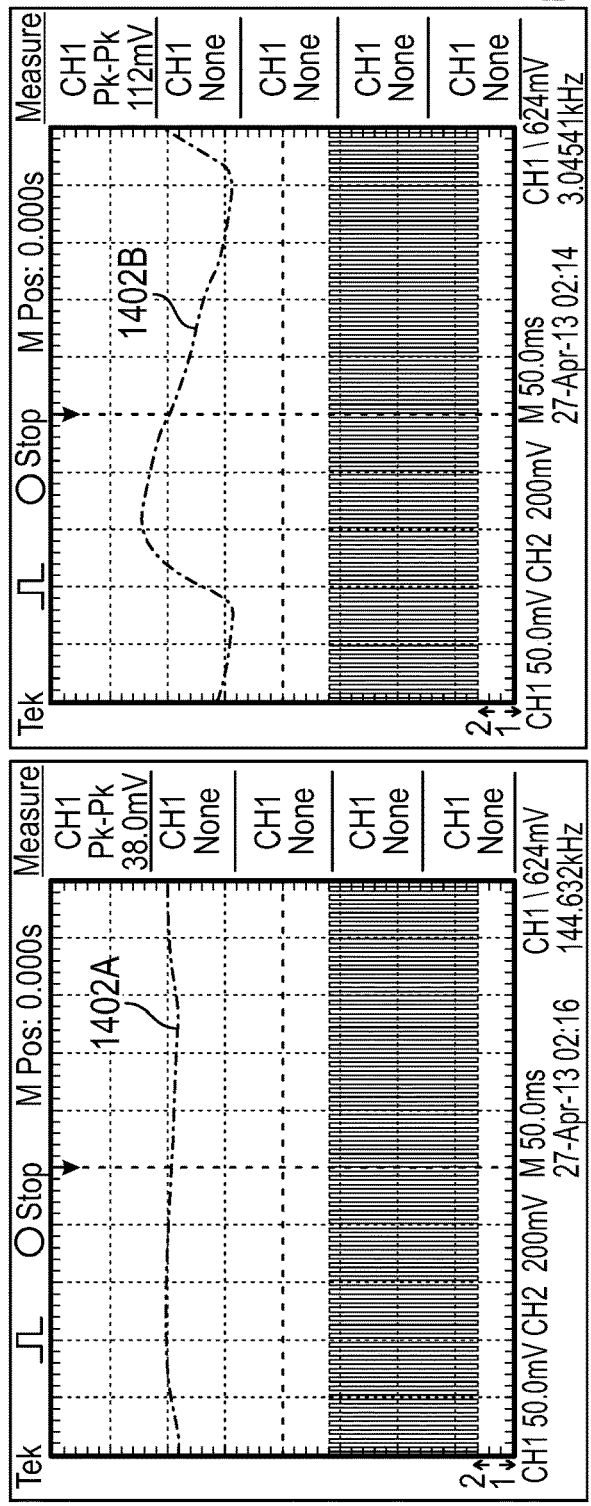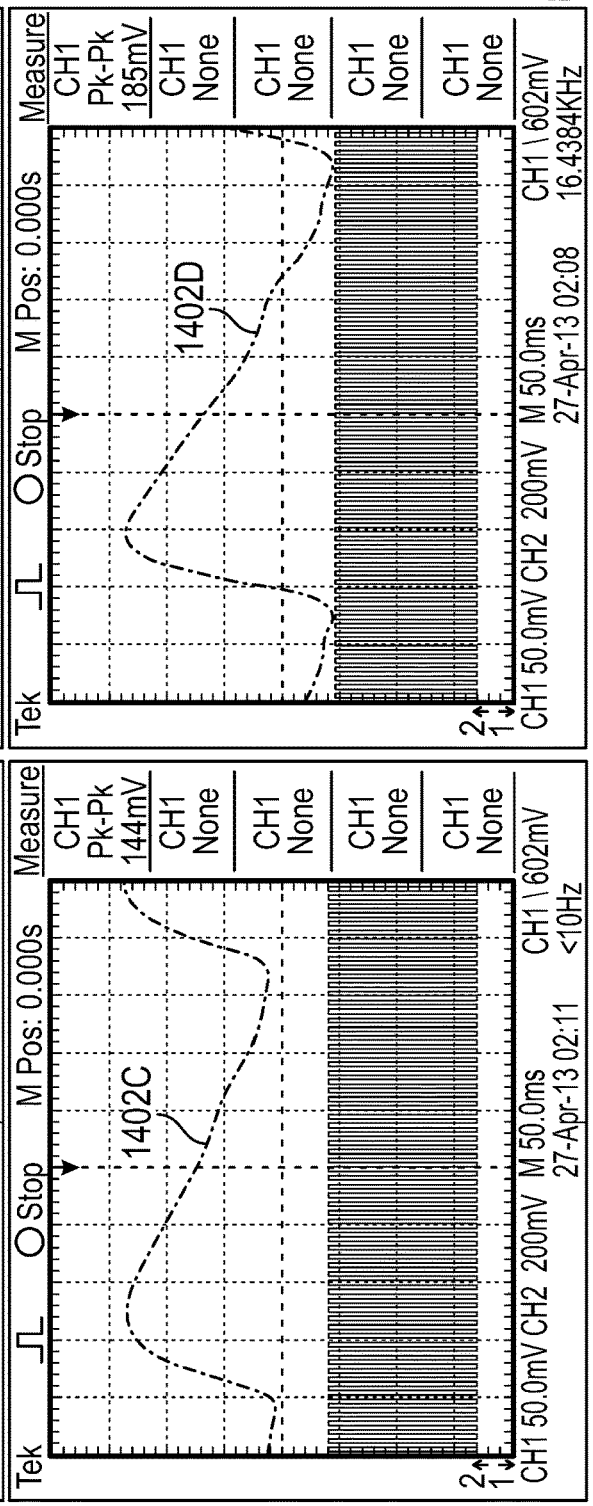
FIG. 14A
FIG. 14B
FIG. 14C
FIG. 14D

BLOCKAGE AND LEAK DETECTION IN MULTIPLE DRESSING REDUCED PRESSURE WOUND THERAPY SYSTEMS

CROSS-REFERENCE TO RELATED APPLICATIONS

This application is a U.S. national stage application of International Patent Application No. PCT/EP2019/072365, filed Aug. 21, 2019, which claims the benefit of U.K. Patent Application No. 1814158.0, filed Aug. 31, 2018, each of which is hereby incorporated by reference in its entirety.

TECHNICAL FIELD

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

BACKGROUND

Many different types of wound dressings are known for aiding in the healing process of a human or animal. These different types of wound dressings include many different types of materials and layers, for example, pads such as gauze pads and/or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

BRIEF DESCRIPTION OF THE DRAWINGS

Embodiments of the present disclosure will now be described hereinafter, by way of example only, with reference to the accompanying drawings in which:

FIGS. 14A-14D illustrate graphs of peak-to-trough pressure signals according to some embodiments.

SUMMARY

Figure 1:
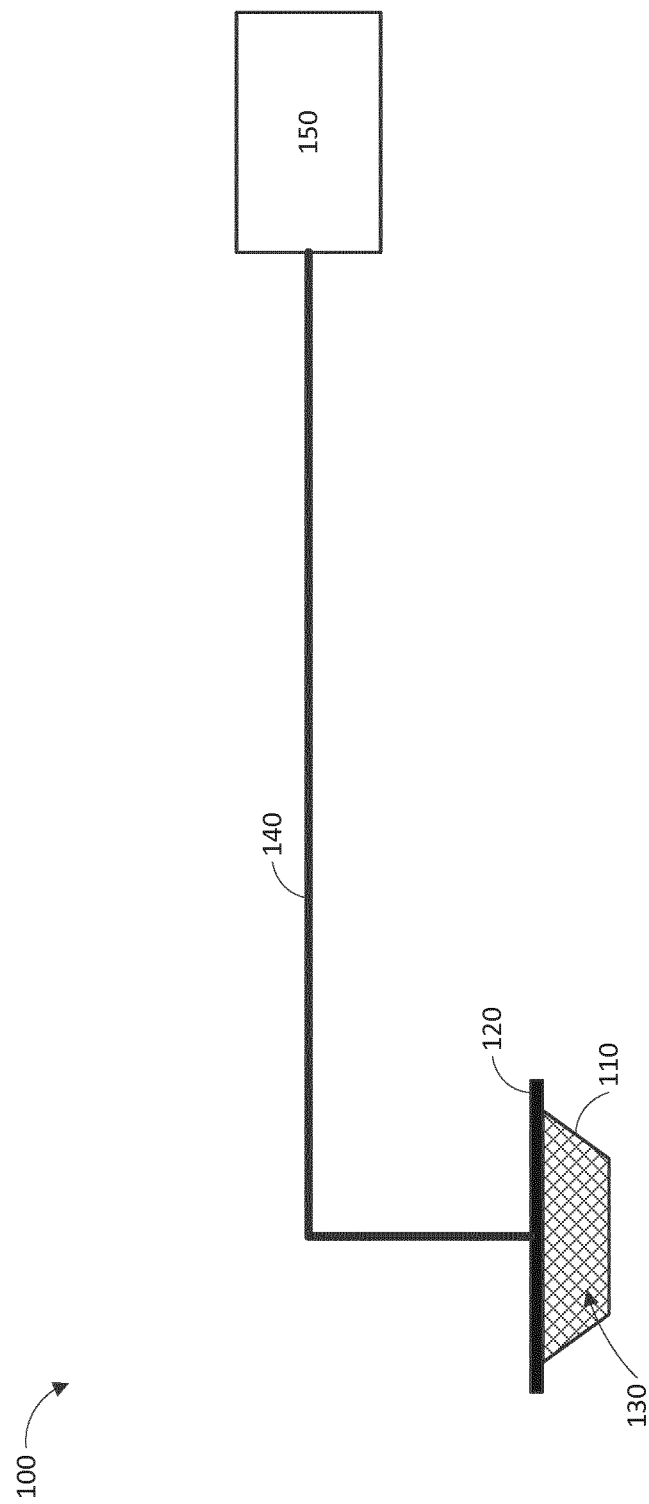
FIG. 1 illustrates a reduced pressure wound therapy system (a TNP system) according to some embodiments.

A negative pressure wound therapy apparatus can include a negative pressure source configured to couple, via a plurality of fluid flow paths, to a plurality of wound dressings and provide negative pressure to the plurality of wound dressings. The plurality of fluid flow paths can include a first fluid flow path configured to fluidically connect a first wound dressing to the negative pressure source, the first wound dressing with a first fluid retention capacity and a second fluid flow path configured to fluidically connect a second wound dressing to the negative pressure source, the second wound dressing with a second fluid retention capacity. The apparatus can include at least one pressure sensor configured to measure pressure associated with the plurality of fluid flow paths and a controller configured to operate the negative pressure source. The controller can be further configured to receive a plurality of pressure measurements from the at least one pressure sensor, determine from at least some of the plurality of pressure measurements first and second fluid retention capacities of the first and second wound dressings, determine a blockage threshold based at least in part on the determined first and second fluid retention capacities, detect presence of a blockage in at least one of the first or second fluid flow paths based at least in part on comparing at least some of the pressure measurements associated with flow of fluid in at least one of the first or second fluid flow paths to the blockage threshold, and provide an indication of the blockage in response to determining that the blockage threshold is satisfied.

The apparatus of any of the preceding paragraphs can include one or more of the following features. Blockage can indicate that at least one of the first or second wound dressings contains an amount of fluid that is greater than a capacity threshold but less than the first or second fluid retention capacity. The controller can be further configured to determine the first and second fluid retention capacities of the first and second wound dressings based on a duration of time for achieving a negative pressure setpoint following activation of the negative pressure source. The controller can be further configured to deactivate the negative pressure source when the negative pressure setpoint has been achieved. The duration of time can be inversely proportional to a combined first and second fluid retention capacities of the first and second wound dressing. The controller can be further configured to detect a combined first and second fluid retention capacities of the first and second wound dressing. The controller can be further configured to determine a rate of pressure change in the first and second fluid flow paths based on at least some of the pressure measurements and determine the first and second fluid retention capacities of the first and second wound dressings based on the rate of pressure change. The rate of pressure change can be inversely proportional to dressing capacity.

The apparatus of any of the preceding paragraphs can include one or more of the following features. The controller can be configured to determine at least one peak-to-trough pressure measurement and detect presence of the blockage based on comparing the at least one peak-to-trough pressure measurement to the blockage threshold. The blockage can be caused by at least one of the first or second dressing being substantially filled with exudate. The controller can be further configured to determine a leak threshold based at least in part on the determined first and second fluid retention capacities, detect presence of a leak in at least one of the first or second fluid flow paths based at least in part on comparing at least some of the pressure measurements associated with flow of fluid in at least one of the first or second fluid flow paths to the leak threshold, and provide an indication of the leak in response to determining that the leak threshold is satisfied. The apparatus can be canisterless.

A method of operating a negative pressure wound therapy apparatus can include, by a controller of the negative pressure wound therapy apparatus, operating a negative pressure source of the negative pressure wound therapy apparatus, wherein the negative pressure source is configured to couple, via a plurality of fluid flow paths, to a plurality of wound dressings, the plurality of fluid flow paths including a first fluid flow path configured to fluidically connect a first wound dressing to the negative pressure source, the first wound dressing with a first fluid retention capacity and a second fluid flow path configured to fluidically connect a second wound dressing to the negative pressure source, the second wound dressing with a second fluid retention capacity. The method can further include, by the controller, receiving a plurality of pressure measurements from the at least one pressure sensor of the negative pressure wound therapy apparatus, determining from at least some of the plurality of pressure measurements first and second fluid retention capacities of the first and second wound dressings, determining a blockage threshold based at least in part on the determined first and second fluid retention capacities, detecting presence of a blockage in at least one of the first or second fluid flow paths based at least in part on comparing at least some of the pressure measurements associated with flow of fluid in at least one of the first or second fluid flow paths to the blockage threshold, and providing an indication of the blockage in response to determining that the blockage threshold is satisfied.

The method of any of the preceding paragraphs can include one or more of the following features. Blockage can indicate that at least one of the first or second wound dressings contains an amount of fluid that is greater than a capacity threshold but less than the first or second fluid retention capacity. The method can further include, by the controller, determining the first and second fluid retention capacities of the first and second wound dressings based on a duration of time for achieving a negative pressure setpoint following activation of the negative pressure source. The method can further include, by the controller, deactivating the negative pressure source when the negative pressure setpoint has been achieved. The duration of time can be inversely proportional to a combined first and second fluid retention capacities of the first and second wound dressing. The method can further include, by the controller, detecting a combined first and second fluid retention capacities of the first and second wound dressing.

The method of any of the preceding paragraphs can include one or more of the following features. The method can further include, by the controller, determining a rate of pressure change in the first and second fluid flow paths based on at least some of the pressure measurements and determining the first and second fluid retention capacities of the first and second wound dressings based on the rate of pressure change. The rate of pressure change can be inversely proportional to dressing capacity. The method can further include, by the controller, determining at least one peak-to-trough pressure measurement and detect presence of the blockage based on comparing the at least one peak-to-trough pressure measurement to the blockage threshold. Blockage can be caused by at least one of the first or second dressing being substantially filled with exudate. The method can further include, by the controller, determining a leak threshold based at least in part on the determined first and second fluid retention capacities, detecting presence of a leak in at least one of the first or second fluid flow paths based at least in part on comparing at least some of the pressure measurements associated with flow of fluid in at least one of the first or second fluid flow paths to the leak threshold, and providing an indication of the leak in response to determining that the leak threshold is satisfied. The negative pressure wound therapy apparatus can be canisterless.

DETAILED DESCRIPTION

Overview

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (for example, −40 mmHg is less than −60 mmHg). Negative pressure that is "more" or "greater" than —X mmHg corresponds to pressure that is further from atmospheric pressure (for example, −80 mmHg is more than −60 mmHg). Local ambient atmospheric pressure can be used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

FIG. 1 illustrates of a negative or reduced pressure wound treatment (or TNP) system 100 including a wound filler 130 placed inside a wound cavity 110, the wound cavity sealed by a wound cover 120 according to some embodiments. The wound filler 130 in combination with the wound cover 120 can be referred to as wound dressing. A flow path 140, such as a single or multi lumen tube or conduit, is connected to the wound cover 120 with a negative pressure wound therapy device, for example pump assembly 150, configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

The pump assembly 150 can provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first time duration, and upon expiration of the first time duration, negative pressure at high setpoint can be delivered for a second time duration. Upon expiration of the second time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

Figure 4A:
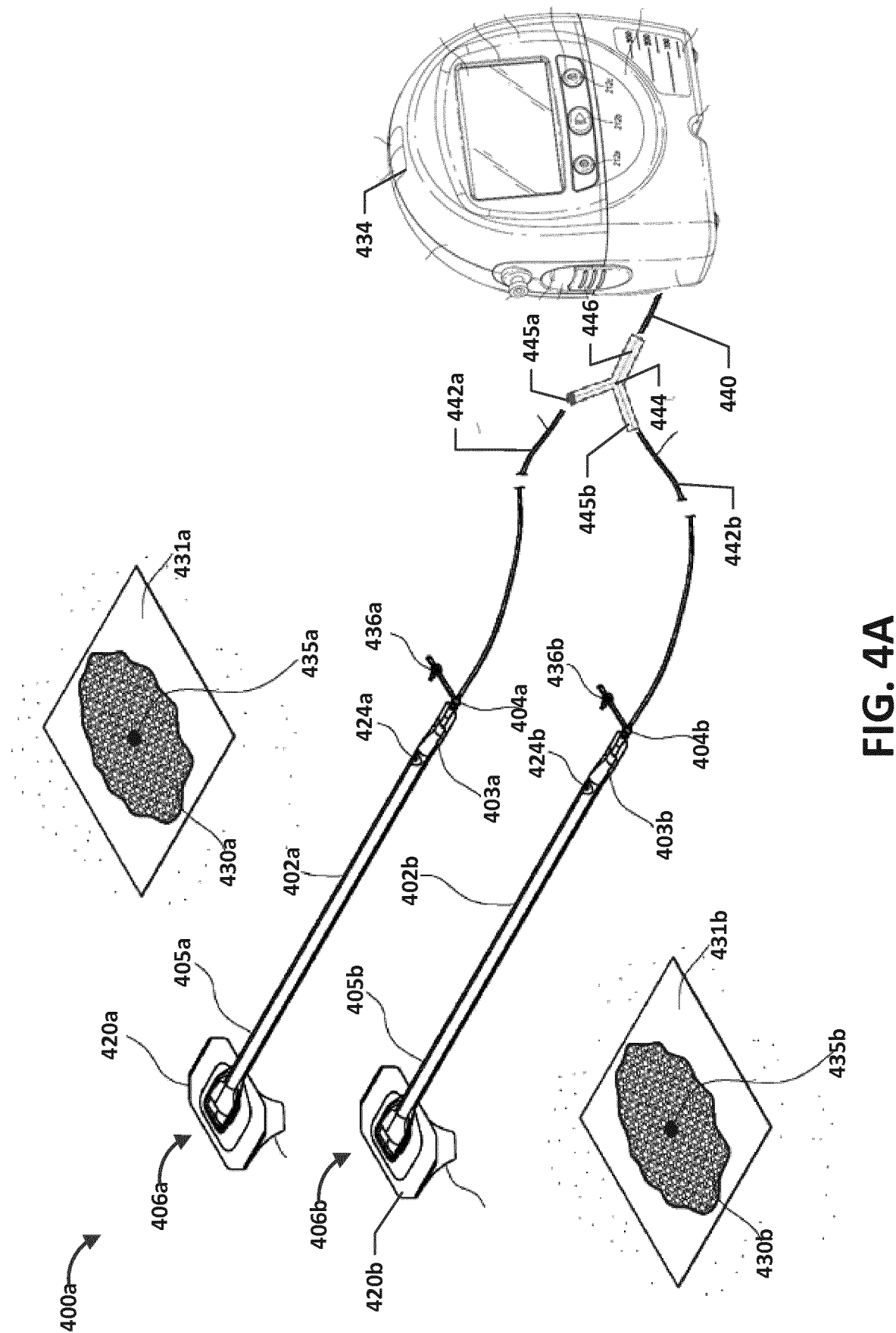
FIGS. 4A and 4B illustrate TNP systems including a pump assembly and canister and illustrating flexible suction adapters being applied to multiple wounds according to some embodiments.
Figure 4B:
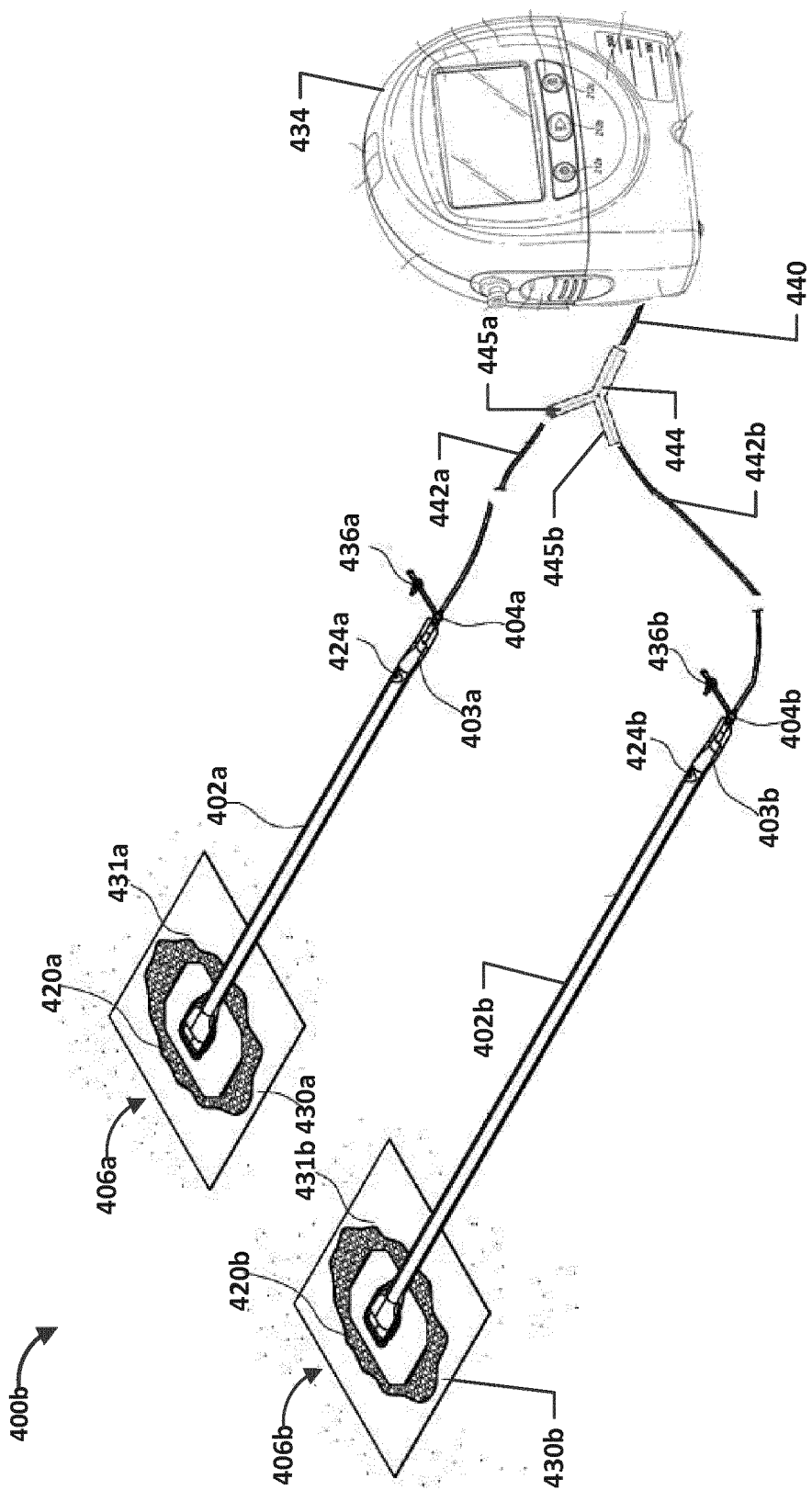

The TNP system 100 moreover can include multiple wound dressings connected to the pump assembly 150, such as described in greater detail with respect to FIGS. 4A and 4B. The performance and wound healing capabilities (such as, fluid management) of the TNP system 100 with multiple wound dressings with the pump assembly 150 can be equivalent to or exceed that of a standard single wound dressing with single pump set-up.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (for example, wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico dressings available from Smith & Nephew. Any of the dressings described herein can be used with Smith and Nephew's Renasys Soft Port connector or interface between the dressing and the pump assembly. For example, Renasys Soft Port connector can be positioned in the flow path 140 and serve as a port for the wound dressing. In other embodiments, other suitable wound dressings can be utilized.

Pump Assembly and Canister

Figure 2:
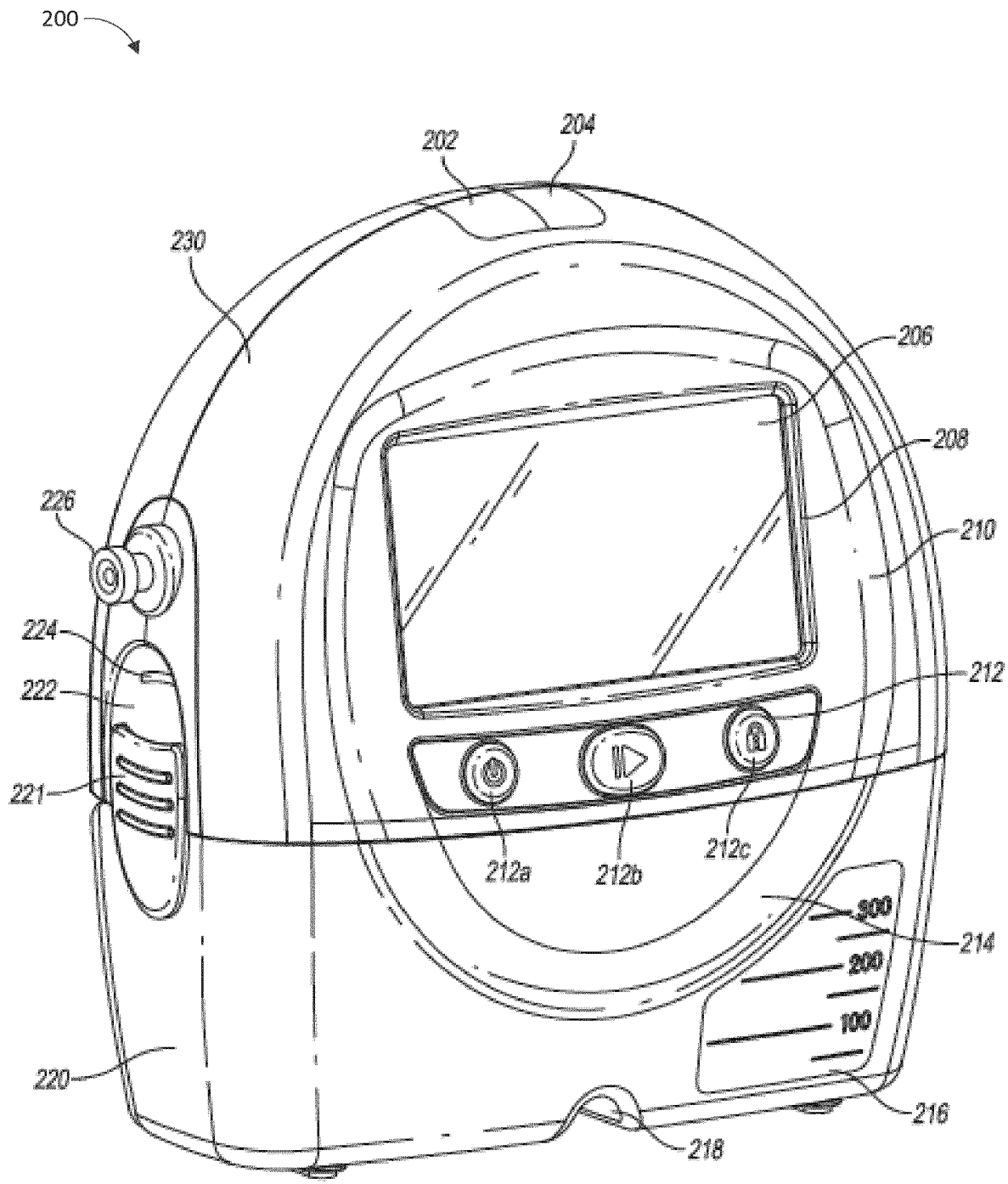
FIG. 2 illustrates a pump assembly having a canister according to some embodiments.

FIG. 2 illustrates a pump assembly 230 having a canister 220 according to some embodiments. As is illustrated, the pump assembly 230 and the canister can be connected, thereby forming a TNP device or system. The pump assembly 230 can be similar to or the same as the pump assembly 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, no flow condition, canister full condition, or any other similar or suitable conditions or combinations thereof. The pump assembly 230 can include additional indicators. The pump assembly can use a single indicator or multiple indicators. Any suitable indicator can be used such as visual, audio, tactile, vibration, indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. The display 206 can render a number of screens or graphical user interfaces (GUIs) for configuring, controlling, and monitoring the operation of the TNP system. The pump assembly 230 includes a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons 212 configured to allow the user to operate and monitor the operation of the TNP system. As is illustrated, there buttons 212a, 212b, and 212c (collectively referred to as buttons 212) are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 includes an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various features are omitted or various additional features are added to the pump assembly 230.

The canister 220 is configured to hold fluid (for example, exudate) removed from the wound cavity 110. The canister 220 includes one or more latches 221 for attaching the canister to the pump assembly 230. In the illustrated embodiment, the canister 220 includes two latches 221 on the sides of the canister. The exterior of the canister 220 can formed from frosted plastic so that the canister is substantially opaque and the contents of the canister and substantially hidden from plain view. The canister 220 includes a gripping portion 214 formed in a case of the canister. The canister 220 includes a substantially transparent window 216, which can also include graduations of volume. The canister 220 includes a tubing channel 218 for connecting to the conduit 140. In some embodiments, one or more of these features, such as the gripping portion 214, are omitted or various additional features are added to the canister 220. Any of the disclosed canisters may include or may omit a solidifier.

While FIG. 2 illustrates a system with a canister, as discussed above with respect to different TNP system embodiments, a pump assembly may be canisterless. Further, some embodiments with a canister may be configured to operate in canisterless mode by detaching the canister. For example, the pump assembly 230 may operate in canisterless mode by detaching the canister 220 and essentially collecting exudate in the dressings or transferring the exudates to another location other than the canister 220.

Electronics and Software

Figure 3A:
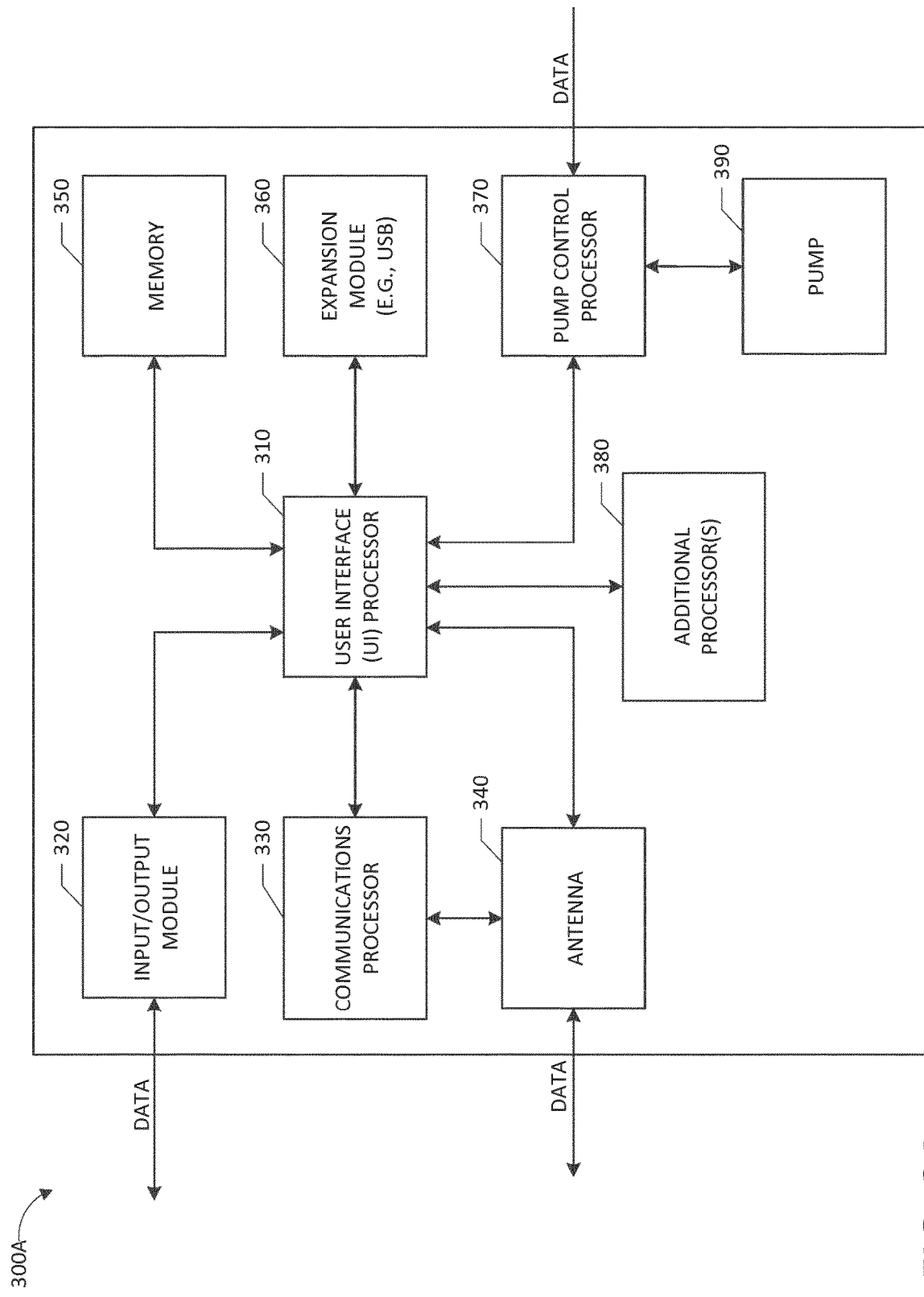
FIG. 3A illustrates an electrical component schematic of a pump assembly according to some embodiments.

FIG. 3A illustrates an electrical component schematic 300A of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. For example, one processor can be responsible for user activity, and another processor can be responsible for controlling the pump. This way, the activity of controlling the pump, which may necessitate a higher level of responsiveness (and corresponding to higher risk level), can be offloaded to a dedicated processor and, thereby, will not be interrupted by user interface tasks, which may take longer to complete because of interactions with the user.

The pump assembly can include a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (for example, processor for controlling the display 206, processor for controlling the buttons 212, etc.). The processor 310 can run a suitable operating system, such as a Linux, Windows CE, VxWorks, etc.

The processor 310, alone or in combination with one or more other processors, can track and store various data, such as one or more of positioning data, therapy parameters, logs, device data, and so on. Data can be stored, for example, in the memory 350.

The pump control processor 370 can be configured to control the operation of a negative pressure source or pump 390. The pump 390 can be a suitable pump, such as a diaphragm pump, peristaltic pump, rotary pump, rotary vane pump, scroll pump, screw pump, liquid ring pump, pump (for example, diaphragm pump) operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control an actuator, such as a pump motor, so that a desired level of negative pressure is achieved in the wound cavity 110. The desired level of negative pressure can be pressure set or selected by the user. In various embodiments, the pump control processor 370 controls the pump actuator (for example, pump motor) using pulse-width modulation (PWM). A control signal for driving the pump actuator can be a 0-100% duty cycle PWM signal. The pump control processor 370 can perform flow rate calculations and detect various conditions in a flow path. The pump control processor 370 can communicate information to the processor 310. The pump control processor 370 can include internal memory or can utilize memory 350. The pump control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (for example, 2G, 3G, LTE, 4G), Wi-Fi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. The pump assembly can include a SIM card, and SIM-based positional information can be obtained.

The communications processor 330 can communicate information to the processor 310. The communications processor 330 can include internal memory or can utilize memory 350. The communications processor 330 can be a low-power processor.

Using the connectivity provided by the communications processor 330, the device can upload any of the data stored, maintained, or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, power source level, etc.; device location information; patient information; and so on. The device can also download various operational data, such as therapy selection and parameters, firmware and software patches and upgrades, and the like.

Figure 3B:
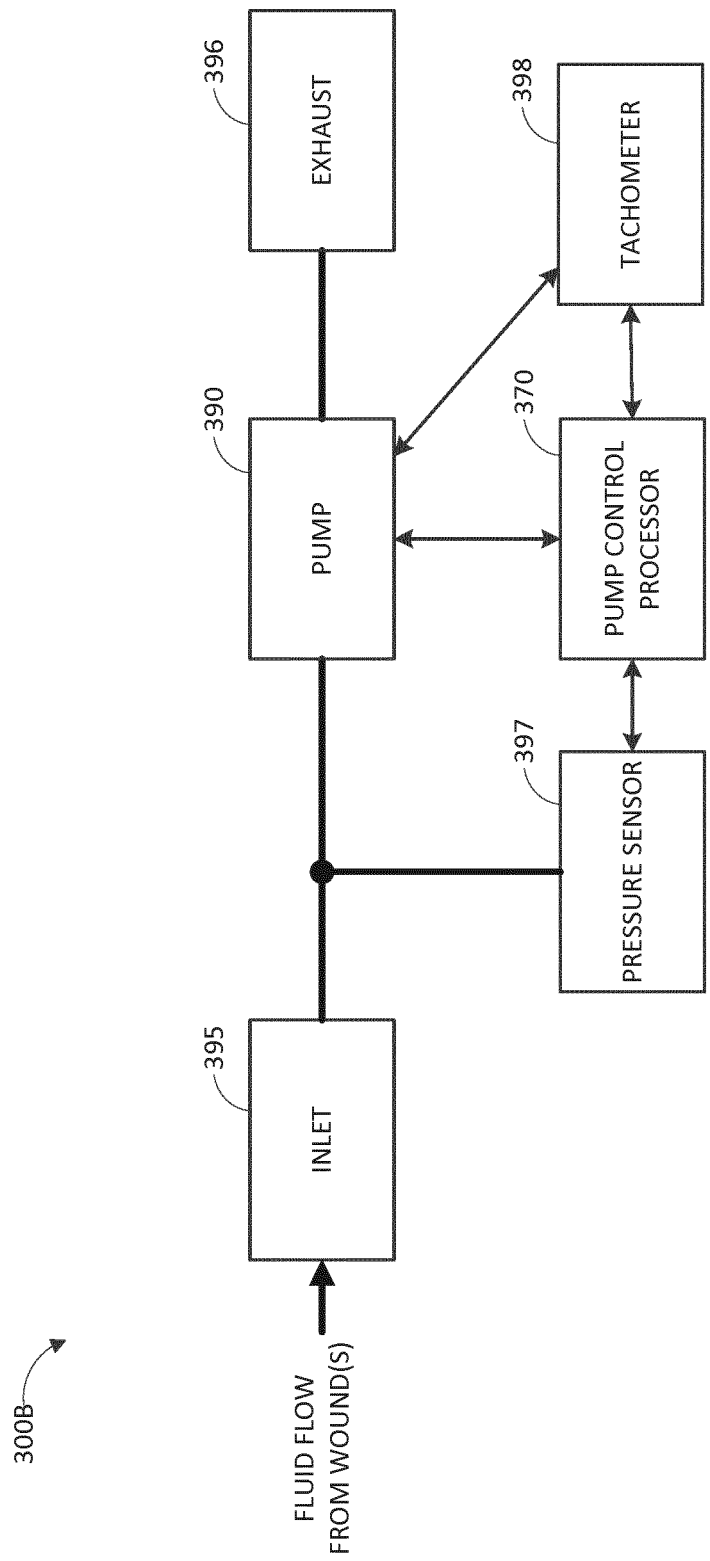
FIG. 3B illustrates a block diagram of certain components of a pump assembly according to some embodiments.

FIG. 3B illustrates a block diagram of certain components 300B of a pump assembly, such as the pump assembly 230, according to some embodiments. The components 300B can include an inlet 395 (which can be similar to or the same as the inlet 252), the pump 390, an exhaust 396, a pressure sensor 397, and the pump control processor 370. The pump assembly of FIG. 3B can include some of the components of the pump assembly of FIG. 3A.

The pump 390 can provide negative pressure in one or more fluid flow paths connecting the pump 390 (via the inlet 395) to one or more wound dressings placed over one or more wounds, such that the negative pressure is communicated through the inlet 395 to one or more fluid flow paths and the respective one or more wound dressings.

In some embodiments, the pump control processor 370 can determine the pressure at the inlet 395 or at any other location in the one or more fluid flow paths using data received from one or more pressure sensors, such as the pressure sensor 397 and control the pump 390 based on the determined pressure. The pump control processor 370 can, for instance, control one or more pump actuators, such as a pump motor of the pump 390, so that a desired level of pressure is achieved at the wound. The desired level of pressure (or pressure setpoint) can be a pressure set or selected by the user or set automatically according to a mode of operation or setting for the pump assembly.

The components 300B can further include one or more additional sensors (not shown), such as a tachometer 398, positioned to detect or determine a level of activity of the pump 390 (for example, the pump motor) and provide indications responsive to the level of activity of the pump 390 to the pump control processor 370. For example, a tachometer 398 can be separate from the pump 390 (for example, external to the pump) and positioned near or coupled to the pump 390, and the tachometer 398 can detect a rotation (such as a partial rotation, complete rotation, or multiple partial or complete rotations) of the pump motor of the pump 390.

In some implementations, one or more pressure sensors can be positioned in or fluidically connected to the one or more fluid flow paths to permit measurement of the pressure in the one or more fluid flow paths. The pressure measurements can be used to determine one or more of rate of change in pressure over time, minimum and maximum pressure, or peak-to-trough (or peak-to-peak) pressure differential. In some implementations, at least two pressure sensors can be positioned at different locations in the fluid flow path to provide differential pressure measurements. For example, a first pressure sensor can be positioned downstream of the wound dressing (such as at or near an inlet of the pump assembly) and a second pressure sensor can be positioned to detect pressure at or near the wound dressing or at or near a canister. This configuration can be accomplished by incorporating, in addition to one or more lumens forming a first fluid flow path connecting the pump assembly to the wound, a second fluid flow path that includes one or more lumens connecting the pump assembly to the wound dressing and through which the second pressure sensor can monitor pressure at or near the wound dressing or at or near the canister. The first and second fluid flow paths can be fluidically isolated from each other. When the at least two pressure sensors are used, the rate of change of pressure, peak-to-trough pressure, peak-to-peak pressure, maximum pressure, or the like in the first and second fluid flow paths can be determined and the difference in pressure detected between the first and second pressure sensors can be determined. These values, measured or derived, can be used separately or together to detect various operational conditions, such as leaks, blockages, canister full, presence of blood in the first fluid flow path or the second fluid flow path, etc. Additionally or alternatively, the values can be used to detect sizes of one or more connected wound dressings. Moreover, multiple redundant pressure sensors can be provided to protect against failure of one or more of the pressure sensors in some implementations.

Multiple Dressing Wound Therapy

FIGS. 4A and 4B illustrate multiple dressing TNP systems 400a, 400b according to some embodiments. The multiple dressing TNP systems 400a, 400a may include a TNP device 434 capable of supplying negative pressure. The TNP device 434 can be similar to or the same as a combination of the pump assembly 230 and the canister 220.

The TNP device 434 may be in fluidic connection with wound dressings 406a, 406b so as to supply negative pressure to wounds 430a, 430b. The fluidic connections between the wound dressings 406a, 406b and the TNP device 434 can be referred to as fluid flow paths (for example, the paths through which fluid aspirated from the wounds flow). For instance, one fluid flow path can include components providing fluidic connection from the TNP device 434 to the wound dressing 406a. This fluid flow path can include the path from the first wound dressing 406a to an inlet of a branching attachment 444 in fluidic connection with the TNP device 434. The multiple dressing TNP system 400a can include the wound dressings 406a, 406b (and corresponding fluid flow paths) in fluidic connection with the TNP device 434 via a plurality of connectors, such as Smith & Nephew's Renasys Soft Port connectors.

Each of the wound dressings 406a, 406b and the corresponding fluid flow paths can include a variety of features or elements which match or are similar to features or elements of another wound dressing or fluid flow path the multiple dressing TNP systems 400a, 400b. Moreover, for brevity and although not described in detail in some instances, features or elements described herein that are denoted with a common number but different letter may have similar or the same features as one another.

The multiple dressing TNP system 400a may include a Renasys Soft Port connector including a bridge 402a having a proximal end 403a and a distal end 405a and an applicator 420a at the distal end 405a of the bridge 402a forming a flexible suction interface or adapter. A connector 404a can be disposed at the proximal end 403a of the bridge 402a to provide fluidic connection between the wound dressing 406a and the TNP device 434. A cap 436a may be provided with the multiple dressing TNP system 400a (and can in some cases, as illustrated, be attached to the connector 404a). The cap 436a can be useful in preventing fluids from leaking out of the proximal end 403a when the connector 404a is disconnected from the TNP device 434. The wound dressings 406 may, in some implementations, collect the wound exudates and other fluids, and the TNP device 434 may not include a canister. In other implementations, multiple canisters are provided, for instance, one canister per wound dressing. The TNP device 434 can in one example be a Renasys Touch device, as manufactured by Smith & Nephew.

The bridge 402a can include upper and lower channel layers (not shown) for channeling wound exudate away from the wound 430a and for transmitting negative pressure or vented air to the wound 430a. The upper and lower channel layers can be elongate layers extending from the proximal end 403a to the distal end 405a and may each include a porous material, such as open-celled foams like polyethylene or polyurethane. One or more of the upper and lower channel layers may include a fabric, such as a knitted or woven spacer fabric or a nonwoven material. Suitable materials may also include terry-woven or loop-pile materials. The fibers may not necessarily be woven, and can include felted and flocked fibrous materials. The upper channel layer is optional, and the multiple dressing TNP system 400a may instead be provided with an open upper channel.

The multiple dressing TNP system 400a can be the same as the multiple dressing TNP system 400b except that the multiple dressing TNP system 400b illustrates the flexible suction adapters placed over the wounds 430a, 430b.

The applicator 420a can be placed over an aperture 435a formed in a drape 431a that is placed over the wound 430a, which may in some cases be filled with a wound packing material such as foam or gauze. Subsequently, with the TNP device 434 connected via a lumen or tube 440 or an inlet manifold branching attachment or connector 444 and a tube 442a to the connector 404a, the TNP device 434 can be activated thereby supplying negative pressure to the wound 430a, as well as in a similar manner to the wound 406b. Application of negative pressure may be applied until a desired level of wound healing is achieved.

Although two wounds and wound dressings are illustrated in the multiple dressing TNP systems 400a, 400b, the TNP device 434 can provide treatment to more than two wounds in some embodiments. Moreover, an air leak 424a (sometimes referred to as a fluid leak or a controlled air leak) may be disposed in a fluid flow path, such as, at the proximal end 403a of the bridge 402a. As described herein, in some embodiments, the bridge 402a, the proximal end 403a, the connector 404a, the distal end 405a, the applicator 420a, the air leak 424a, the drape 431a, the aperture 435a, the cap 436a, and the tube 442a can respectively be or function the same as a bridge 402b, a proximal end 403b, a connector 404b, a distal end 405b, an applicator 420b, an air leak 424b, a drape 431b, an aperture 435b, a cap 436b, and a tube 442b.

Branching Attachment

The TNP device 434 can be in fluidic connection with the wound dressings 406a, 406b via the tubes 440, 442a, 442b, the bridges 402a, 402b, and an inlet manifold branching attachment 444. As illustrated in FIGS. 4A-4B, the inlet manifold branching attachment 444 can connect the TNP device 434 to a plurality of fluid flow paths via dressing conduit attachment portions 445a, 445b. The inlet manifold branching attachment 444 can further include any number of additional dressing conduit attachment portions to be fluidically connected to a negative pressure attachment portion 446 via a joint. In some embodiments, the manifold branching attachment 444 can be connected directly to the TNP device 434 without using the tube 440.

The negative pressure attachment portion 446 can, in some implementations, include multiple different attachment portions. Each of the attachment portions can include a shaft extending away from the joint and an inlet distal the joint. The multiple inlets can be configured to fluidically connect to the TNP device 434. For instance, the inlets can include male or female non-luer connectors to attach to a corresponding male or female connector of a conduit or the TNP device 434.

The inlet manifold branching attachment 444 can include one or more incorporated valves, clamps, caps, air leaks, or other flow regulator mechanisms which may be configured to admit fluid into a fluid flow path or, alternatively, block or restrict flow or passage of fluid through a fluid flow path. In some embodiments, valves, air leaks, or other flow regulation mechanisms in the inlet manifold branching attachment 444 can be opened or closed electronically. A controller of the TNP device 434 can, for instance, communicate with the valves, air leaks, etc. to open or close each one individually or as a unit. This communication can be wired or wireless.

The dressing conduit attachment portions 445a, 445b can include shafts forming the top portions of a Y—(two wound), W—(three wound) or other shape of the inlet manifold branching attachment. The proximal ends of dressing conduit shafts and the distal end of the pump conduit shaft can meet at a joint. In some implementations, the joint can include a hinge that allows rotation of the shafts about the joint. The inlet manifold branching attachment 444 can further be a W-shaped connector in some implementations, and the inlet manifold branching attachment 444 can include three or more dressing conduit attachment portions and one negative pressure attachment portion.

The inlet manifold branching attachment can include rigid plastic or flexible plastic tubing and can also or alternatively be encased in a soft silicone sleeve to increase patient comfort and prevent the inlet manifold branching attachment 444 from becoming a pressure point.

The TNP device 434 can aspirate fluid from wounds 430a, 430b simultaneously when the inlet manifold branching attachment 444 attaches the TNP device 434 to the wound dressings 406a, 406b. The performance and wound healing capabilities (such as, fluid management) of such a system can be equivalent to or exceed that of a standard single wound dressing with single pump set-up.

An integrated inlet manifold (not shown) can be used in place of the inlet manifold branching attachment 444 in some implementations. In implementations such as these, inlet manifolds can be incorporated (for example, directly attached) into the TNP device 434 such that the one or more fluid flow paths can fluidically connect to the TNP device 434 via one or more inlets of the integrated inlet manifolds. The integrated inlet manifolds can include a splitting attachment (similar to the Y-shaped or W-shaped branching attachment described herein) or can include one or more separately integrated inlets in fluidic connection with the TNP device 434.

Figure 5:
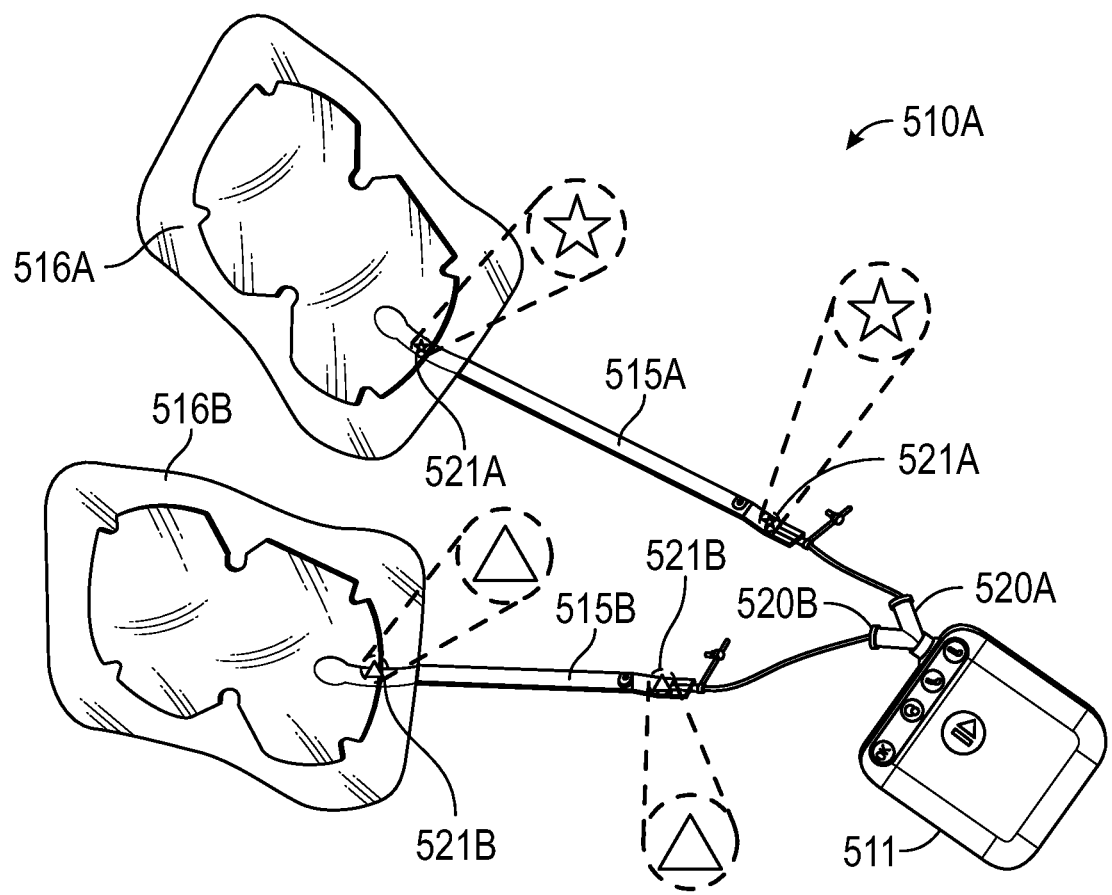
FIG. 5 illustrates another embodiment of multiple dressing TNP system.

FIG. 5 illustrates another embodiment of multiple dressing TNP system 510. The multiple dressing TNP system 510 includes a TNP apparatus 511, a first fluid flow path 515A, a first wound dressing 516A, a second fluid flow path 515B, a second wound dressing 516B, a plurality of integrated inlet manifolds or connectors 520A, 520B. The TNP apparatus 511 can be a canisterless system. The plurality of integrated inlet manifolds 520A, 520B are integrated with the TNP apparatus 511 and are fluidically connected to the first wound dressing 516A via the first fluid flow path 515A and the second wound dressing 516B via the second fluid flow path 515B.

In some instances, a fluid flow path 515A can be lengthy and in a location remote from the TNP apparatus 511. As such, it can be desirable for the fluid flow paths to include one or more indicators 521A, 521B (collectively 521) which would be helpful to a user in identifying which fluid flow path 515A is connected to a particular inlet of the plurality of integrated inlet manifolds 520A, 520B.

As shown, the first fluid flow path 515A includes a plurality of first identifiers (stars) 521A, and the second fluid flow path 515A includes a plurality of second identifiers (triangles) 521B. In both instances, at least one identifier 521 is located in close proximity to the inlet manifolds 520A, 520B and at least one identifier is located in close proximity to a wound dressing. In some examples, a fluid flow path can include more than two identifiers 521. For example, identifiers 521 can be located across the length of the fluid flow path. Moreover, an identifier 521 can alternatively include a printed glyph, a printed icon, an embossed glyph, an embossed icon, a braille character, a color-coding and the like. In some examples, an electronically controlled indication (such as an LED, an indicator on a display, etc.) is associated with each fluid flow path. This facilitates the apparatus 511 in indicating an operating condition that may have occurred on the associated dressing.

In some embodiments, at least one pressure sensor can be positioned with an inlet manifold (either an integrated manifold or attachment manifold) to measure the combined pressure of the first and second fluid flow paths. The controller of the TNP apparatus 511 monitors the pressure measured by the pressure sensor and determines whether an operating condition has occurred in any of the fluid flow paths. In some aspects, the controller can be configured to provide a first indication associated with an operating condition in the first fluid flow path 515A and a second indication associated with an operating condition in the second fluid flow path 515B.

In some examples, a negative pressure therapy system includes more than two wound dressings. Accordingly, the number of fluids flow paths and inlets can correspond with the number of wound dressings. For instance, a negative pressure therapy system having four wound dressings can have at least four fluid flow paths and at least four inlets manifolds. In some examples, a single wound dressing can be configured to communicate with a TNP apparatus via more than one fluid flow path. In some examples, the negative pressure therapy system can include more inlets manifolds than fluid flow paths or wound dressings. In examples such as these, the additional inlets can be disregarded or plugged.

Figure 6:
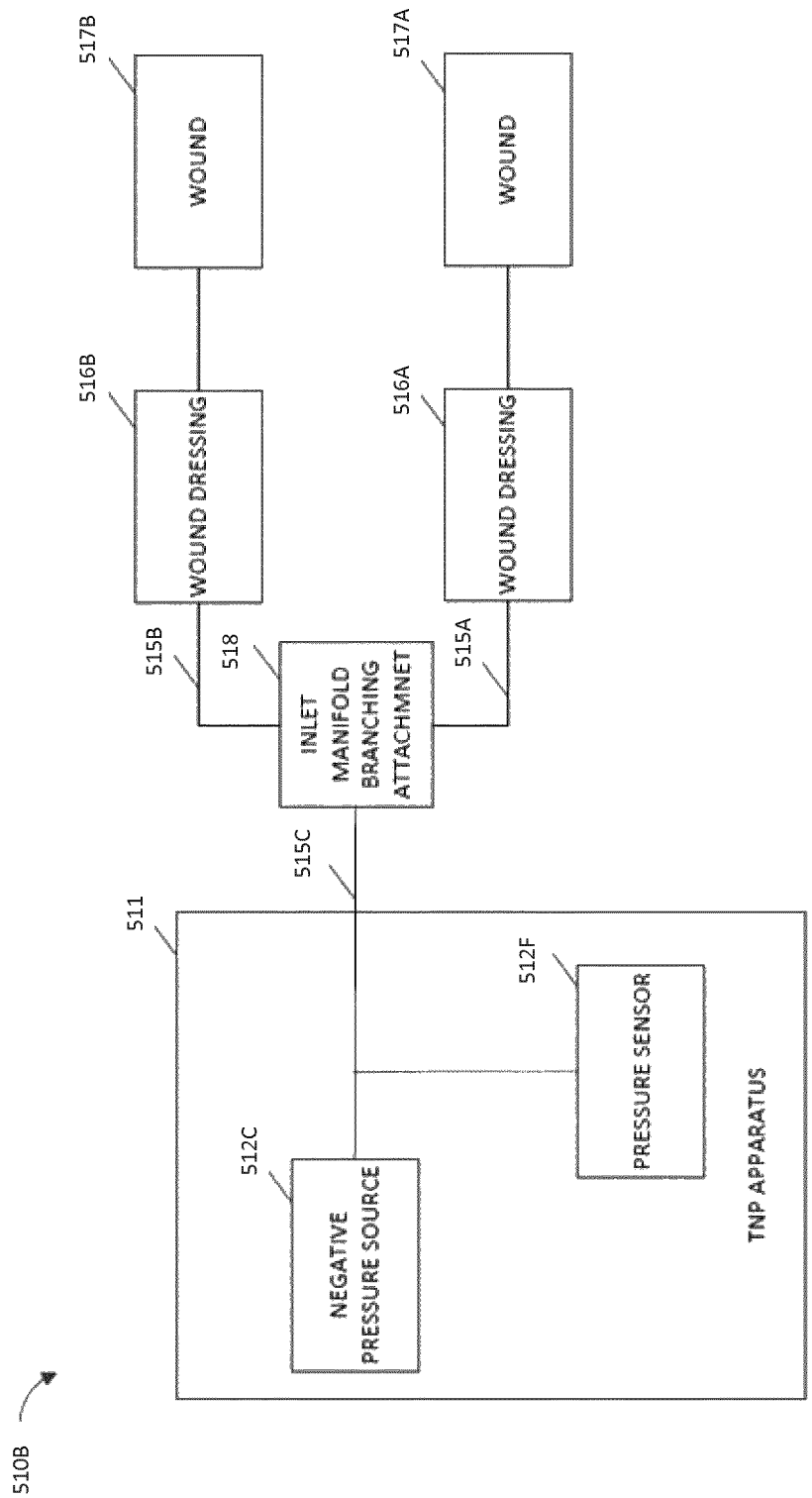
FIG. 6 illustrates a TNP system that includes a pump assembly as well as an inlet manifold branching attachment, pressure sensor and a plurality of fluid flow paths, wound dressings positioned over wounds according to some embodiments.

FIG. 6 illustrates a block diagram of multiple dressing TNP system, according to some embodiments. The system 510B includes the TNP apparatus 511 of FIG. 1, as well as a first fluid flow path 515A, a first wound dressing 516A configured to be placed over a first wound 517A, a second fluid flow path 515B, a second wound dressing 516B configured to be placed over a second wound 517B, an inlet manifold branching attachment 518, and a third fluid flow path 515C. The TNP apparatus 511 can be used to treat the first wound 517A using the first wound dressing 16A that is in fluidic communication with the TNP apparatus 511 via the first fluid flow path 15A, the inlet manifold branching attachment 518, and the third fluid flow path 515C. The TNP apparatus 511 can also be used to treat the second wound 517B using the second wound dressing 516B that is in fluidic communication with the TNP apparatus 511 via the second fluid flow path 515B, the inlet manifold branching attachment 518, and the third fluid flow path 515C.

The inlet manifold branching attachment 18 is attached between the TNP apparatus 511 and the first and second wound dressings, thereby advantageously enabling the TNP apparatus 511 to generate and maintain negative pressure in or under both of the wound dressings simultaneously. In this example, the inlet manifolds are not incorporated into the TNP apparatus. Instead, an inlet manifold branching attachment 518, such as a Y-shaped connector, is used to connect the first and second fluid flow paths 515A-515B to the third fluid flow path 515C. In other examples, inlet manifolds can be incorporated into the TNP apparatus 511 such that the first and second fluid flow paths connect directly to the TNP apparatus via integrated inlet manifolds.

A pressure sensor 512F is positioned in the third fluid flow path 515C, such as at or near an inlet of the TNP apparatus 511, to measure pressure in the third fluid flow path 515C. The controller of the TNP apparatus 511 can monitor the pressure measured by the pressure sensor 512F and determine whether an operating condition (for example, a blockage, leakage, overpressure, or dressing full condition) has occurred in within the negative pressure therapy system 5108.

In some instances, the controller can determine that an operating condition exists by comparing the measured pressure to an expected measured pressure (or flow). An "expected" pressure (or flow) can be the pressure measured by a pressure sensor in a negative pressure system operating in a normal state. The expected pressure can be equivalent or almost equivalent (for example, within 1, 2, 3, 4, 5, 10, 15, or 20 mmHg) to a pressure supplied by the negative pressure source (or a pressure selected by a user). In contrast, an "unexpected" pressure (or flow) can be any measured pressure other than the expected pressure (or flow). For instance, in some examples, a wound dressing experiencing a blockage, overpressure, or dressing full condition, can cause the pressure sensor to measure a higher (for example, more negative pressure) than expected pressure. In other examples, a wound dressing experiencing a leakage condition can cause the pressure sensor to measure a lower than expected pressure. In some examples, an operating condition can change the measured pressure (for example, cause a spike, dip, increase, or decrease in measured pressure). In some embodiments, measured pressure is compared to one or more thresholds in order to determine if it is expected or unexpected.

In some examples, the TNP apparatus 511 will only function (for example, provide negative pressure) when two or more wound dressings are connected. Additionally, some indicators or functionality of the TNP apparatus that is available when only a single wound dressing is connected may be disabled so as not to confuse the user. For example, in some instances the dressing full indicator may not be available for TNP systems having more than one connected wound dressing. Thus, the dressing full indicator(s) can be disabled or removed from the front panel so as not to confuse the user with unavailable functionality.

In any of the disclosed embodiments, the connected wound dressings may be of different sizes. For example, multiple large wound dressings or multiple small wound dressings may be connected to the TNP apparatus 434 or 511. In some embodiments, the connected wound dressings may be of the same size.

Wound Dressings

Figure 7:
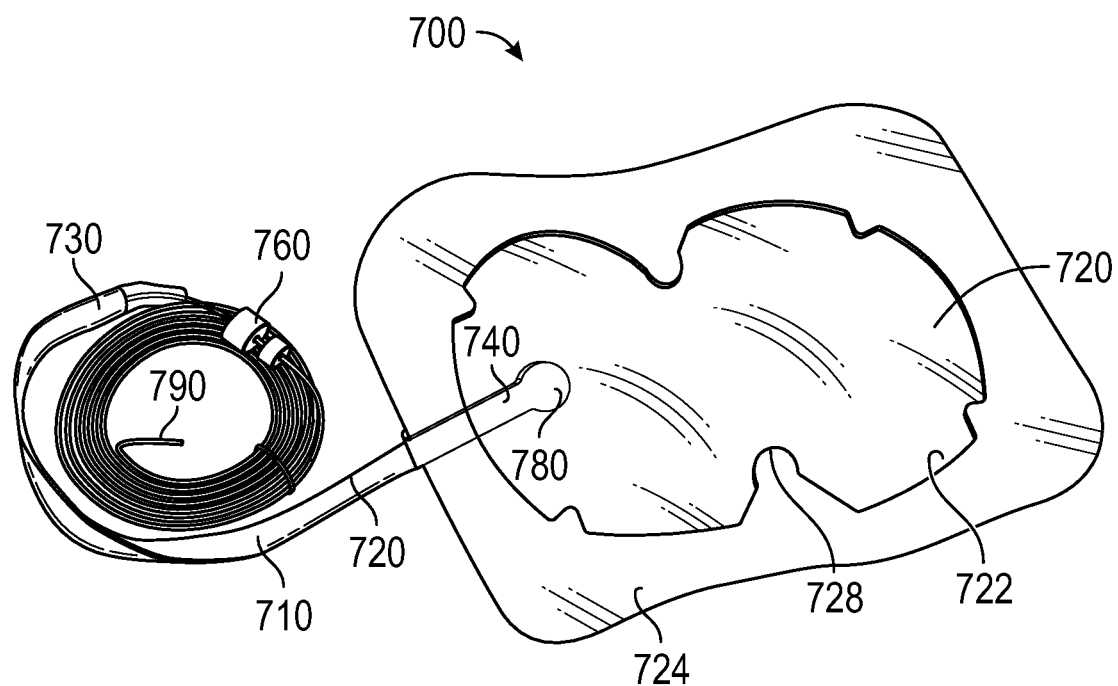
FIG. 7 illustrates a wound dressing according to some embodiments.

FIG. 7 illustrates a perspective view of a wound dressing 700 in conjunction with a fluidic connector 710 according to some embodiments. The illustrated wound dressing can be used with any of the embodiment of negative pressure systems described herein. As is illustrated, the wound dressing 700 has an oval shaped absorbent layer 720 having multiple lobes 722. In some embodiments, the absorbent layer 720 can have six lobes. In some examples, two or more lobes 722 (such as, six lobes) are provided on the wound dressing 700; the lobes 722, and specifically, the gaps between the lobes 722, aid the wound dressing 700 in conforming to nonplanar wounds. For example, it may be advantageous to use the dressing 700 to conform around joints such as elbows and knees. The dressing 700 can have a rectangular or square shaped backing layer 724, and in some embodiments, the dressing 700 may come in different sizes as described herein.

In some examples, the dressing 700 may also have circular cutouts 728 in a central waisted portion, which may be located along a midline of the dressing 700 transverse to a longitudinal axis of the dressing 700. Such cutouts 728 may be, in some embodiments, 10 mm, or approximately 10 mm, in diameter, or may be in the range of 5 mm to 25 mm, or approximately 5 mm to approximately 25 mm, in diameter. As illustrated, the circular cutouts 728 can be symmetrically arranged on opposite sides of a longitudinal midline of the dressing 700, and may form an arc of greater than 180 degrees, sometimes between 180 and 270 (or about 180 to 270) degrees.

As illustrated, the fluidic connector 710 may include an elongate conduit, or a bridge 720 having a proximal end 730 and a distal end 740, and an applicator 780 at the distal end 740 of the bridge 720. In some examples, the bridge 720 provides a soft, fluidic connection between the tube 790 and the wound dressing 700 and can advantageously distance the tube 790 from wound dressing 700, thereby reducing the potential for pressure points caused by the tube 790. In some examples, the length of the bridge 720 can be 20, 30, 45, 60, or 70 centimeters (+/−a few centimeters). An optional coupling 760 can be disposed at the proximal end 730 of the bridge 720. In some examples, a cap (not shown) can be attached to the coupling 760 and can be useful in preventing fluids from leaking out of the proximal end 730.

A negative pressure system (such as the one illustrated in FIG. 12) may be connected to the coupling 760 via a tube 790 (such as by connecting the tube 790 to one of the connectors 21A or 21B), or the system may be connected directly to the coupling 760 or directly to the bridge 720. In some embodiments, as FIGS. 4A-4B and 5 illustrate, more than one wound dressings 700 can be coupled with a negative pressure source via a manifold branching attachment 444 or a plurality of integrated inlet manifolds or connectors 520A, 520B. In use, the dressing 700 is placed over a suitably-prepared wound, which may in some cases be filled with a wound packing material such as foam or gauze. The applicator 780 of the fluidic connector 710 has a sealing surface that is placed over an aperture in the dressing 700 and is sealed to the top surface of the dressing 700. Either before, during, or after connection of the fluidic connector 710 to the dressing 700, a system is connected via the tube 790 to the coupling 760, or is connected directly to the coupling 760 or to the bridge 720. The system is then activated, thereby supplying negative pressure to the wound. Application of negative pressure may be applied until a desired level of healing of the wound is achieved. In some embodiments, the system can be miniaturized and portable, although larger conventional pumps may also be used with the dressing 700. In some embodiments, the system may be attached or mounted within, onto, or adjacent the dressing 700.

In some embodiments, a source of negative pressure (such as a pump) and some or all other components of a TNP system, such as power source(s), sensor(s), connector(s), user interface component(s) (such as button(s), switch(es), speaker(s), screen(s), etc.) and the like, can be integral with the wound dressing 700. The wound dressing 700 can include a cover layer for positioning over the layers of the wound dressing. The cover layer can be the upper most layer of the dressing. In some embodiments, the wound dressing 700 can include a second cover layer for positioning over the layers of the wound dressing and any of the integrated components. The second cover layer can be the upper most layer of the dressing or can be a separate envelope that encloses the integrated components of the topical negative pressure system.

As shown in FIG. 7, the fluidic connector 710 includes an enlarged distal end, or head 740 that is in fluidic communication with the dressing 700 as will be described in further detail below. In one embodiment, the enlarged distal end has a round or circular shape. The head 740 is illustrated here as being positioned near an edge of the dressing 700, but may also be positioned at any location on the dressing. For example, some embodiments may provide for a centrally or off-centered location not on or near an edge or corner of the dressing 700. In some embodiments, the dressing 700 may include two or more fluidic connectors 710, each having one or more heads 740, in fluidic communication therewith. In some embodiments, the head 740 may measure 30 mm along its widest edge. The head 740 forms at least in part the applicator 780, described above, that is configured to seal against a top surface of the wound dressing.

Figure 8:
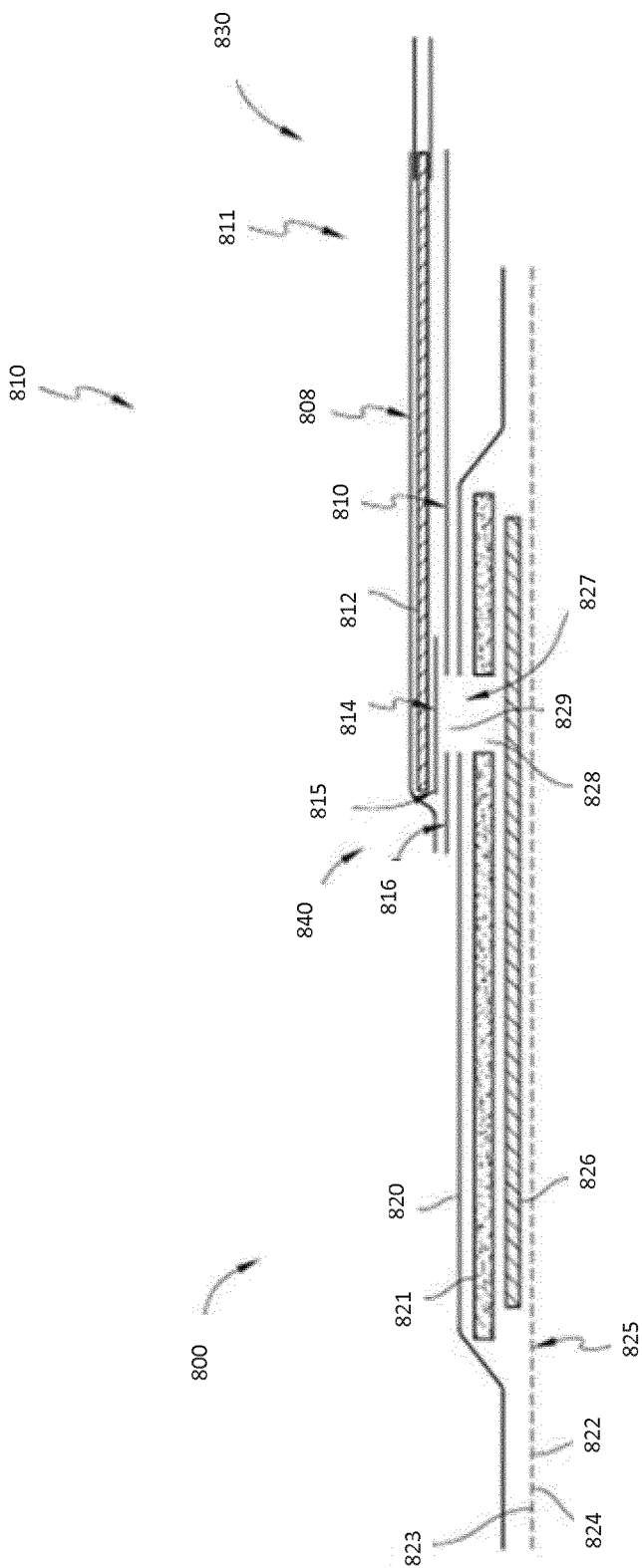
FIG. 8 illustrates a cross section of a fluidic connector connected to a wound dressing according to some embodiments.

FIG. 8 illustrates a cross-section through a wound dressing 800 similar to the wound dressing 700 as shown in FIG. 7 along with fluidic connector 810 according to some embodiments. The wound dressing 800, which can alternatively be any wound dressing embodiment disclosed herein or any combination of features of any number of wound dressing embodiments disclosed herein, can be located over a wound site to be treated. The dressing 800 can be used with any of the negative pressure system embodiment described herein. The dressing 800 may be placed as to form a sealed cavity over the wound site. In some embodiments, the dressing 800 includes a top or cover layer, or backing layer 820 attached to an optional wound contact layer 822, both of which are described in greater detail below. These two layers 820, 822 can be joined or sealed together to define an interior space or chamber. This interior space or chamber may include additional structures that may be adapted to distribute or transmit negative pressure, store wound exudate and other fluids removed from the wound, and other functions that will be explained in detail below. Examples of such structures, described below, include a transmission layer 826 and an absorbent layer 821.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 8, the wound contact layer 822 can be a polyurethane layer or polyethylene layer or other flexible layer which is perforated, for example via a hot pin process, laser ablation process, ultrasound process or in some other way or otherwise made permeable to liquid and gas. The wound contact layer 822 has a lower surface 824 and an upper surface 823. The perforations 825 can include through holes in the wound contact layer 822 that enable fluid to flow through the layer 822. The wound contact layer 822 helps prevent tissue ingrowth into the other material of the wound dressing. The perforations can be small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 822 may help maintain the integrity of the entire dressing 800 while also creating an airtight seal around the absorbent pad in order to maintain negative pressure at the wound.

Some embodiments of the wound contact layer 822 may also act as a carrier for an optional lower and upper adhesive layer (not shown). For example, a lower pressure sensitive adhesive may be provided on the lower surface 824 of the wound dressing 800 whilst an upper pressure sensitive adhesive layer may be provided on the upper surface 823 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 800 to the skin around a wound site. In some embodiments, the wound contact layer may include perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 826 of porous material can be located above the wound contact layer 822. This porous layer, or transmission layer, 826 allows transmission of fluid including liquid and gas away from a wound site into upper layers of the wound dressing. In particular, the transmission layer 826 can ensure that an open air channel can be maintained to communicate negative pressure over the wound area even when the absorbent layer 821 has absorbed substantial amounts of exudates. The layer 826 can remain open under the typical pressures that will be applied during negative pressure wound therapy as described above, so that the whole wound site sees an equalized negative pressure. The layer 826 may be formed of a material having a three dimensional structure. For example, a knitted or woven spacer fabric (for example Baltex 7970 weft knitted polyester) or a non-woven fabric could be used.

In some embodiments, the transmission layer 826 includes a 3D polyester spacer fabric layer including a top layer (that is to say, a layer distal from the wound-bed in use) which is a 84/84 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 821 helps lock the liquid away or itself wicks the liquid onwards towards the cover layer where it can be transpired.

To improve the liquid flow across the transmission layer 826 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 821 of absorbent material is provided above the transmission layer 826. The absorbent material, which includes a foam or non-woven natural or synthetic material, and which may optionally include a super-absorbent material, forms a reservoir for fluid, particularly liquid, removed from the wound site. In some embodiments, the layer 821 may also aid in drawing fluids towards the backing layer 820.

The material of the absorbent layer 821 may also prevent liquid collected in the wound dressing 800 from flowing freely within the dressing, and can act so as to contain any liquid collected within the dressing. The absorbent layer 821 also helps distribute fluid throughout the layer via a wicking action so that fluid is drawn from the wound site and stored throughout the absorbent layer 821. This helps prevent agglomeration in areas of the absorbent layer 821. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 821 may typically be manufactured from ALLEVYN™ foam, Freudenberg 18-224-4 or Chem-Posite™11C-450. In some embodiments, the absorbent layer 821 may include a composite having superabsorbent powder, fibrous material such as cellulose, and bonding fibers. In some embodiments, the composite is an airlaid, thermally-bonded composite.

In some embodiments, the absorbent layer 821 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 827 can be provided in the backing layer 820 to allow a negative pressure to be applied to the dressing 800. The fluidic connector 810 can be attached or sealed to the top of the backing layer 820 over the orifice 827 made into the dressing 800, and communicates negative pressure through the orifice 827. A length of tubing may be coupled at a first end to the fluidic connector 810 and at a second end to a negative pressure system (not shown) to allow fluids to be removed from the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 810 may be adhered and sealed to the backing layer 820 using an adhesive such as an acrylic, cyanoacrylate, epoxy, UV curable or hot melt adhesive. The fluidic connector 810 may be formed from a soft polymer, for example a polyethylene, a polyvinyl chloride, a silicone or polyurethane having a hardness of 30 to 90 on the Shore A scale. In some embodiments, the fluidic connector 810 may be made from a soft or conformable material.

The absorbent layer 821 can include at least one through hole 828 located so as to underlie the fluidic connector 810. The through hole 828 may in some embodiments be the same size as the opening 827 in the backing layer, or may be bigger or smaller. As illustrated in FIG. 8 a single through hole can be used to produce an opening underlying the fluidic connector 810. It will be appreciated that multiple openings could alternatively be utilized. Additionally should more than one port be utilized according to certain embodiments of the present disclosure one or multiple openings may be made in the absorbent layer 821 and the obscuring layer in registration with each respective fluidic connector. Although not essential to certain embodiments of the present disclosure, the use of through holes in the super-absorbent layer may provide a fluid flow pathway which remains unblocked in particular when the absorbent layer is near saturation.

The aperture or through-hole 828 can be provided in the absorbent layer 821 beneath the orifice 827 such that the orifice is connected directly to the transmission layer 826 as illustrated in FIG. 8. This allows the negative pressure applied to the fluidic connector 810 to be communicated to the transmission layer 826 without passing through the absorbent layer 821. This ensures that the absorbent layer does not inhibit the negative pressure applied to the wound site as it absorbs wound exudates. In other embodiments, no aperture may be provided in the absorbent layer 821, or alternatively a plurality of apertures underlying the orifice 827 may be provided. In further alternative embodiments, additional layers may be provided over the absorbent layer 821 and beneath the backing layer 820.

The backing layer 820 can be gas impermeable, but moisture vapor permeable, and can extend across the width of the wound dressing 800. The backing layer 820, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 820 and a wound site where a negative pressure can be established. The backing layer 820 can be sealed to the wound contact layer 822 in a border region around the circumference of the dressing, ensuring that no air is drawn in through the border area, for example via adhesive or welding techniques. The backing layer 820 protects the wound from external bacterial contamination (bacterial barrier) and allows liquid from wound exudates to be transferred through the layer and evaporated from the film outer surface. The backing layer 820 can include two layers; a polyurethane film and an adhesive pattern spread onto the film. The polyurethane film can be moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The absorbent layer 821 may be of a greater area than the transmission layer 826, such that the absorbent layer overlaps the edges of the transmission layer 826, thereby ensuring that the transmission layer does not contact the backing layer 820. This provides an outer channel of the absorbent layer 821 that is in direct contact with the wound contact layer 822, which aids more rapid absorption of exudates to the absorbent layer. Furthermore, this outer channel ensures that no liquid is able to pool around the circumference of the wound cavity, which could seep through the seal around the perimeter of the dressing leading to the formation of leaks. As illustrated in FIG. 8, the absorbent layer 821 may define a smaller perimeter than that of the backing layer 820, such that a boundary or border region is defined between the edge of the absorbent layer 821 and the edge of the backing layer 820.

As shown in FIG. 8, one embodiment of the wound dressing 800 includes an aperture 828 in the absorbent layer 821 situated underneath the fluidic connector 810. In use, for example when negative pressure is applied to the dressing 800, a wound facing portion of the fluidic connector may thus come into contact with the transmission layer 826, which can thus aid in transmitting negative pressure to the wound site even when the absorbent layer 821 is filled with wound fluids. Some embodiments may have the backing layer 820 be at least partly adhered to the transmission layer 826. In some embodiments, the aperture 828 is at least 1-2 mm larger than the diameter of the wound facing portion of the fluidic connector 810, or the orifice 827.

In particular for embodiments with a single fluidic connector 810 and through hole, the fluidic connector 810 and through hole can be located in an off-center position as illustrated in FIG. 7. Such a location may permit the dressing 800 to be positioned onto a patient such that the fluidic connector 810 is raised in relation to the remainder of the dressing 800. So positioned, the fluidic connector 810 and the filter 814 may be less likely to come into contact with wound fluids that could prematurely occlude the filter 814 so as to impair the transmission of negative pressure to the wound site.

Turning now to the fluidic connector 810, some embodiments include a sealing surface 816, a bridge 811 (corresponding to bridge 720) in FIG. 7) with a proximal end 730 and a distal end 740, and a filter 814. The sealing surface 816 can form the applicator previously described that is sealed to the top surface of the wound dressing. In some embodiments a bottom layer of the fluidic connector 810 may include the sealing surface 816. The fluidic connector 810 may further include an upper surface vertically spaced from the sealing surface 816, which in some embodiments is defined by a separate upper layer of the fluidic connector. In other embodiments the upper surface and the lower surface may be formed from the same piece of material. In some embodiments the sealing surface 816 may include at least one aperture 829 therein to communicate with the wound dressing. In some embodiments the filter 814 may be positioned across the opening 829 in the sealing surface, and may span the entire opening 829. The sealing surface 816 may be configured for sealing the fluidic connector to the cover layer of the wound dressing, and may include an adhesive or weld. In some embodiments, the sealing surface 816 may be placed over an orifice in the cover layer. In other embodiments, the sealing surface 816 may be positioned over an orifice in the cover layer and an aperture in the absorbent layer 820, permitting the fluidic connector 810 to provide air flow through the transmission layer 826. In some embodiments, the bridge 811 may include a first fluid passage 812 in communication with a source of negative pressure, the first fluid passage 812 including a porous material, such as a 3D knitted material, which may be the same or different than the porous layer 826 described previously. The bridge 811 can be encapsulated by at least one flexible film layer 808, 810 having a proximal and distal end and configured to surround the first fluid passage 812, the distal end of the flexible film being connected to the sealing surface 816. The filter 814 is configured to substantially prevent wound exudate from entering the bridge.

Some embodiments may further include an optional second fluid passage positioned above the first fluid passage 812. For example, some embodiments may provide for an air leak disposed at the proximal end of the top layer 808 that is configured to provide an air path into the first fluid passage 812 and dressing 800.

The fluid passage 812 can be constructed from a compliant material that is flexible and that also permits fluid to pass through it if the spacer is kinked or folded over. Suitable materials for the fluid passage 812 include without limitation foams, including open-cell foams such as polyethylene or polyurethane foam, meshes, 3D knitted fabrics, non-woven materials, and fluid channels. In some embodiments, the fluid passage 812 may be constructed from materials similar to those described above in relation to the transmission layer 826. Advantageously, such materials used in the fluid passage 812 not only permit greater patient comfort, but may also provide greater kink resistance, such that the fluid passage 812 is still able to transfer fluid from the wound toward the source of negative pressure while being kinked or bent.

In some embodiments, the fluid passage 812 may include a wicking fabric, for example a knitted or woven spacer fabric (such as a knitted polyester 3D fabric, Baltex 7970®, or Gehring 879®) or a nonwoven fabric. These materials selected can be suited to channelling wound exudate away from the wound and for transmitting negative pressure or vented air to the wound site, and may also confer a degree of kinking or occlusion resistance to the fluid passage 812. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may include several layers of material stacked or layered over each other, which may in some cases be useful in preventing the fluid passage 812 from collapsing under the application of negative pressure. In other embodiments, the wicking fabric used in the fluid passage 812 may be between 1.5 mm and 6 mm; or the wicking fabric may be between 3 mm and 6 mm thick, and may include either one or several individual layers of wicking fabric. In other embodiments, the fluid passage 812 may be between 1.2-3 mm thick, for example, thicker than 1.5 mm. Some embodiments, for example a suction adapter used with a dressing which retains liquid such as wound exudate, may employ hydrophobic layers in the fluid passage 812, and only gases may travel through the fluid passage 812. Additionally, and as described previously, the materials used in the system can be conformable and soft, which may help to avoid pressure ulcers and other complications which may result from a wound treatment system being pressed against the skin of a patient.

The filter element 88 can be impermeable to liquids, but permeable to gases, and is provided to act as a liquid barrier and to ensure that no liquids are able to escape from the wound dressing 800. The filter element 814 may also function as a bacterial barrier. Typically the pore size is 0.2 μm. Suitable materials for the filter material of the filter element 814 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids, an oleophobic filter membrane can be used, for example 1.0 micron MMT-332 prior to 0.2 micron MMT-323. This prevents the lipids from blocking the hydrophobic filter. The filter element can be attached or sealed to the port or the cover film over the orifice. For example, the filter element 814 may be molded into the fluidic connector 810, or may be adhered to one or both of the top of the cover layer and bottom of the suction adapter 810 using an adhesive such as, but not limited to, a UV cured adhesive.

It will be understood that other types of material could be used for the filter element 814. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the present disclosure, filter element 814 includes a support layer and an acrylic co-polymer membrane formed on the support layer. The wound dressing 800 according to certain embodiments of the present disclosure can use microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 814 may also include an odor absorbent material, for example activated charcoal, carbon fiber cloth or Vitec Carbotec-RT Q2003073 foam, or the like. For example, an odor absorbent material may form a layer of the filter element 814 or may be sandwiched between microporous hydrophobic membranes within the filter element. The filter element 814 thus enables gas to be exhausted through the orifice. Liquid, particulates and pathogens however are contained in the dressing.

Similar to the embodiments of wound dressings described above, some wound dressings include a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lays a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that includes a liquid-impermeable, gas-permeable semi-permeable membrane (SPM) or filter that overlies the aforementioned apertures.

One or more wound dressing, such as one or more absorbent layers 821, can, over the course of a negative pressure therapy, become saturated with exudate. As exudate accumulates in the one or more wound dressings 800, the effectiveness of the treatment may become compromised. Other compromising operating conditions, such as leakages, blockages, high pressure, or low vacuum, may also develop. Some disclosed embodiments provide systems or methods for the detection and notification of one or more of such operating conditions.

As described herein, the wound dressings may have various sizes including small dressings to large dressings. For example, in case of a rectangular wound dressing (such as the dressing 700), a small wound dressing can be 5 centimeters by 5 centimeters and a large wound dressing can be 15 centimeters by 10 centimeters. Depending on the shape of the wound dressing(s), different size representations can be used including, for example, radius for circular wound dressings. In some instances, the wound dressings can be categorized into certain standardized sizes, such as small, medium, large, extra-large, etc. For example, Pico dressings available from Smith & Nephew are available in the following sizes: 10 cm×20 cm (45 cm$^3$ volume), 10 cm×30 cm (75 cm$^3$ volume), 10 cm×40 cm (105 cm$^3$ volume), or 25 cm×25 cm (240 cm$^3$ volume) among others.

In some cases, each wound dressing may have associated parameters or operational profiles. The TNP system may download, store, or access various parameters or profiles associated with the particular dressing, such as an expected rate of pressure change when operating a pump with a known capacity in a sealed condition. For instance, with a large dressing it can take longer for a pump to reduce pressure down to a negative pressure setpoint than it would take the pump to reduce pressure down to the setpoint in a smaller dressing. This can be due to the larger amount of fluid that would have to be evacuated from a larger dressing that has larger volume that a smaller dressing.

Delivery of Wound Therapy

A pump assembly, such as the pump assembly 200 or 511, can control a vacuum pump to deliver negative pressure therapy to a wound according to a selected or programmed protocol. Pump control can be performed by one or more processors, such as the pump control processor 370 alone or in combination with the processor 310.

For example, the user can select continuous operation at a desired pressure (or negative pressure setpoint). The pump assembly can activate the vacuum pump to reduce or draw down the pressure at the wound (for example, under the dressing) to reach the setpoint. As explained herein, in some embodiments, the drawdown can be performed by increasing the negative pressure at the wound limited by a maximum change in negative pressure per unit time called compression, until the setpoint (or another selected pressure value as explained below) has been achieved. Wound drawdown can be defined as the period of time immediately after therapy has been initiated during which the wound has not yet achieved the setpoint. As explained below, at the end of this period when the setpoint is achieved, the flow rate in the fluid flow path should be below a leak (or high flow) threshold and above a low vacuum threshold, otherwise an appropriate alarm will be activated.

Figure 11:
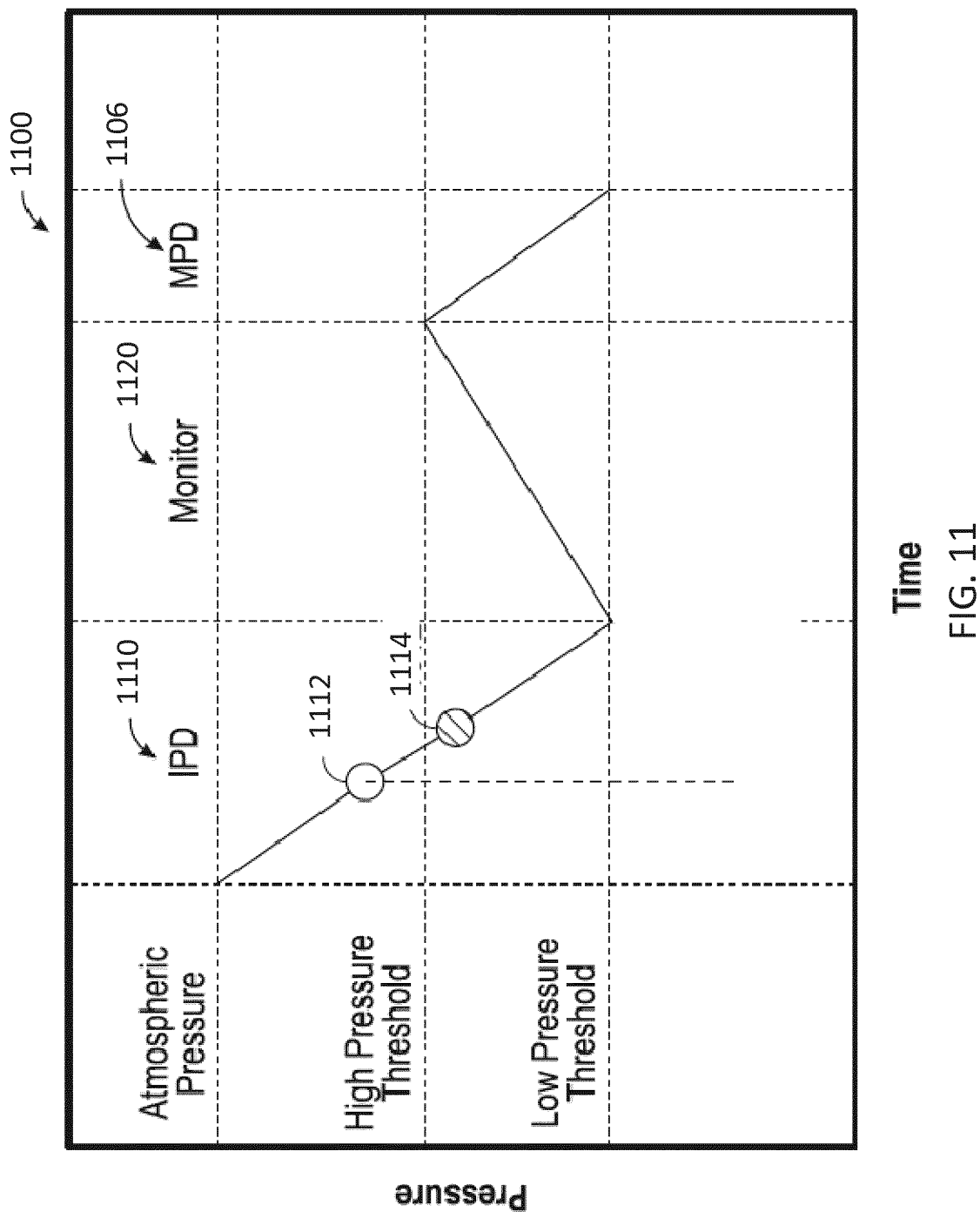
FIG. 11 illustrates pressure versus time graph according to some embodiments.

As another example, the user can select intermittent operation between two desired pressures (or high and low pressure setpoints illustrated in, for example, FIG. 11). The pump assembly can activate the vacuum pump to reduce or draw down the pressure at the wound to reach the low (or more negative) pressure setpoint. Subsequently, the pump assembly can allow pressure at the wound to increase to reach the high (or more positive) pressure setpoint. As explained herein, decreasing and increasing negative pressure can be performed in accordance with the compression setting.

As yet another example, compression can be used anytime there is a change in the pressure setpoint (which can include stopping delivery of negative pressure). In some embodiments, different compression settings can be used for setpoint changes that result in decreasing or increasing pressure at the wound. In various embodiments, compression setting can be adjusted while a pressure setpoint is being achieved.

Figure 9:
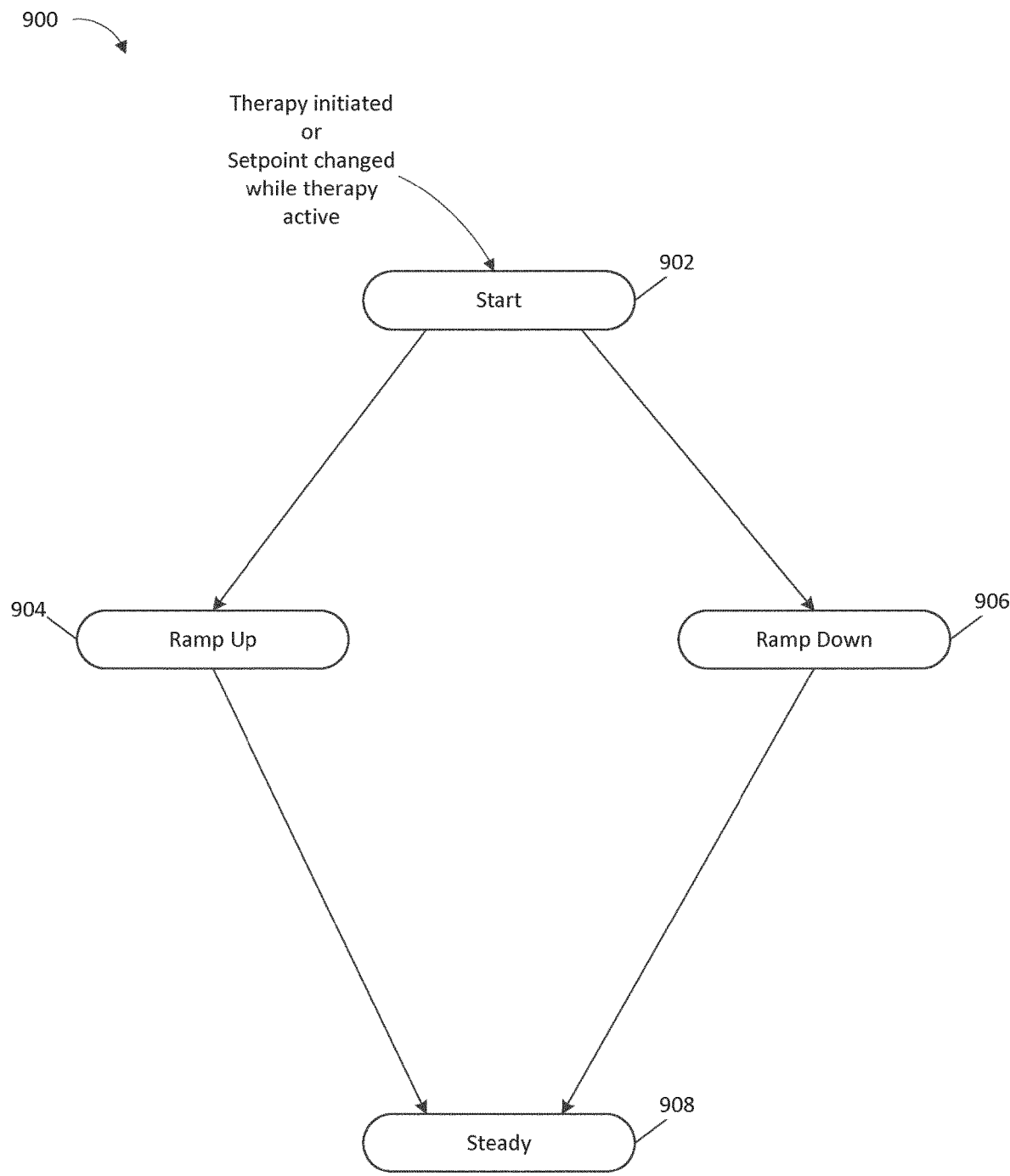
FIG. 9 illustrates a process for providing negative pressure wound therapy according to some embodiments.

FIG. 9 illustrates a process 900 for providing negative pressure wound therapy according to some embodiments. The process 900 can be executed by one or more processors, such as the processor 310 or the pump control processor 370, alone or in combination, and utilize one or more other components described herein or other systems not shown. The process 900 can be periodically executed, such as for example every 100 milliseconds (or 10 times per second) or at any other suitable frequency. Alternatively or additionally, the process 900 can be continuously executed.

The process 900 can begin in block 902, which it can transition to when therapy is initiated or when the setpoint is changed while therapy is being delivered. In block 902, the process 900 compares wound pressure, which can be determined as explained below, to the setpoint. For example, the process 900 can subtract the wound pressure from the setpoint or vice versa. If the wound pressure is below the setpoint, the process 900 can transition to block 904. Conversely, if the wound pressure exceeds or is equal to the setpoint, the process 900 can transition to block 906.

In block 904 (pressure ramp up), the process 900 can increment a pump ramp setpoint by an amount that depends on the compression setting as explained herein. The vacuum pump will then attempt to draw down (or make more negative) the wound pressure to reach the current value of the pump ramp setpoint. For example, a suitable pump drive signal, such as voltage or current signal, can be generated and supplied to the pump motor so as to increase the speed of the pump motor to achieve wound draw down. For purposes of efficiency, the pump motor can be driven using PWM or any other suitable method. The process 900 can continue incrementing the pump ramp setpoint until it reaches the setpoint selected by the user. The process 900 can transition to block 908 when the wound pressure has nearly reached or reached the setpoint, which can correspond to reaching steady state pressure under the wound dressing. For example, the process 900 can transition to block 908 when the wound pressure is within a ramp up threshold pressure of the setpoint, such as within 2 mmHg of the setpoint or within any other suitable value. In some embodiments, the pump ramp setpoint can be adaptively set to a higher negative pressure than the setpoint. For example, as is explained below, the device can detect presence of one or more leaks which result in a higher level of flow. Because this can cause loss of pressure at the wound, the device can compensate such loss of pressure by increasing the pump ramp setpoint above the setpoint. For instance, the device can set the pump ramp setpoint to be 1%, 2%, 5%, etc. more negative than the setpoint. In certain embodiments, the pump ramp setpoint can be adaptively set to a lower negative pressure (or more positive pressure) than the setpoint.

In block 906 (pressure ramp down), the process 900 can set the pump ramp setpoint to the setpoint selected by the user (or to another set value as explained above). The process 900 can deactivate the pump so that the wound pressure is allowed to decay, such as due to one or more leaks in the fluid flow path, to reach or almost reach the setpoint. This can be performed in accordance with the compression setting, such as for example, deactivating the pump for a first period of time and then activating the pump for a second period of time so that pressure at the wound increases according to the compression setting. At this point, the process 900 can transition to block 908. For example, the process 900 can transition to block 908 when the wound pressure is within a ramp down threshold pressure of the setpoint, such as within 9 mmHg of the setpoint or within any other suitable value. In some cases, the ramp down threshold pressure can be the same as the ramp up threshold pressure. In some embodiments, the pump ramp setpoint can be adaptively set to a lower negative pressure than the setpoint. For example, as is explained below, the device can detect presence of one or more leaks which result in a higher level of flow. Because this can cause loss of pressure at the wound, the device can compensate such loss of pressure by decreasing the pump ramp setpoint below the setpoint. For instance, the device can set the pump ramp setpoint to be 1%, 2%, 9%, etc. less negative than the setpoint. In certain embodiments, the pump ramp setpoint can be adaptively set to a higher negative pressure (or more positive pressure) than the setpoint.

In block 908 (steady state), the pump ramp setpoint can be set to the setpoint selected by the user (or another suitable value). The process 900 can control the vacuum pump to maintain the desired negative pressure at the wound. One or more conditions, such as high vacuum, low vacuum, leak, and the like can be detected in block 908 as is explained below. If the user changes the setpoint to be more negative or more positive or if delivery of therapy is paused, the process 900 can transition to block 902.

In some embodiments, the pump assembly controls the vacuum pump to draw down the wound (for example, as is explained herein in connection with block 904) by utilizing compression. Using compression can be beneficial for avoiding rapid changes in wound pressure, which can minimize patient pain or discomfort, reduce noise produced as a result of operating the pump, maintain efficient delivery of negative pressure, maintain efficient use of power (for example, battery power), and the like. Compression can be executed by the process 900, which in turn can be implemented by the reduced pressure control processor 370 alone or in combination with the processor 310. Compression can correspond to the maximum desired increase or decrease in negative pressure at the wound per unit of time. Compression can be determined based on the negative pressure setpoint in the continuous mode or low and high negative pressure setpoints in the intermittent mode and selected compression setting (for example, low, medium, or high).

In some embodiments, the pump assembly monitors various parameters or resulting profiles (for example, see FIGS. 12, 13, and 14A-14D), such as pressure in the fluid flow path(s), rate of change in pressure, rate of flow in the fluid flow path(s), pressure profiles, or the like, in order to control the pump in connection with delivery of negative pressure wound therapy. Parameters monitoring and pump control can be performed by one or more processors, such as the reduced pressure control processor 370 alone or in combination with the processor 310. Monitoring pressure parameters or profiles can be used to ensure that therapy is properly delivered to the wound, to detect wound dressing sizes, leakages, blockages, high pressure, and low vacuum, canister full, or the like.

In additional or alternative embodiments, multiple pressure sensors can be placed in different locations in the fluid flow path(s) to facilitate detection of one or more of the conditions described herein. For example, in addition to or instead of the pressure sensor being placed in the pump inlet, one or more pressure sensors can be placed in the wound or under the dressing to directly determine the wound pressure. Measuring pressure at different locations in the fluid flow path, such as in the canister and at the wound, can facilitate detection of wound dressing sizes, blockages, leaks, canister full condition, leaks, or the like.

Figure 12:
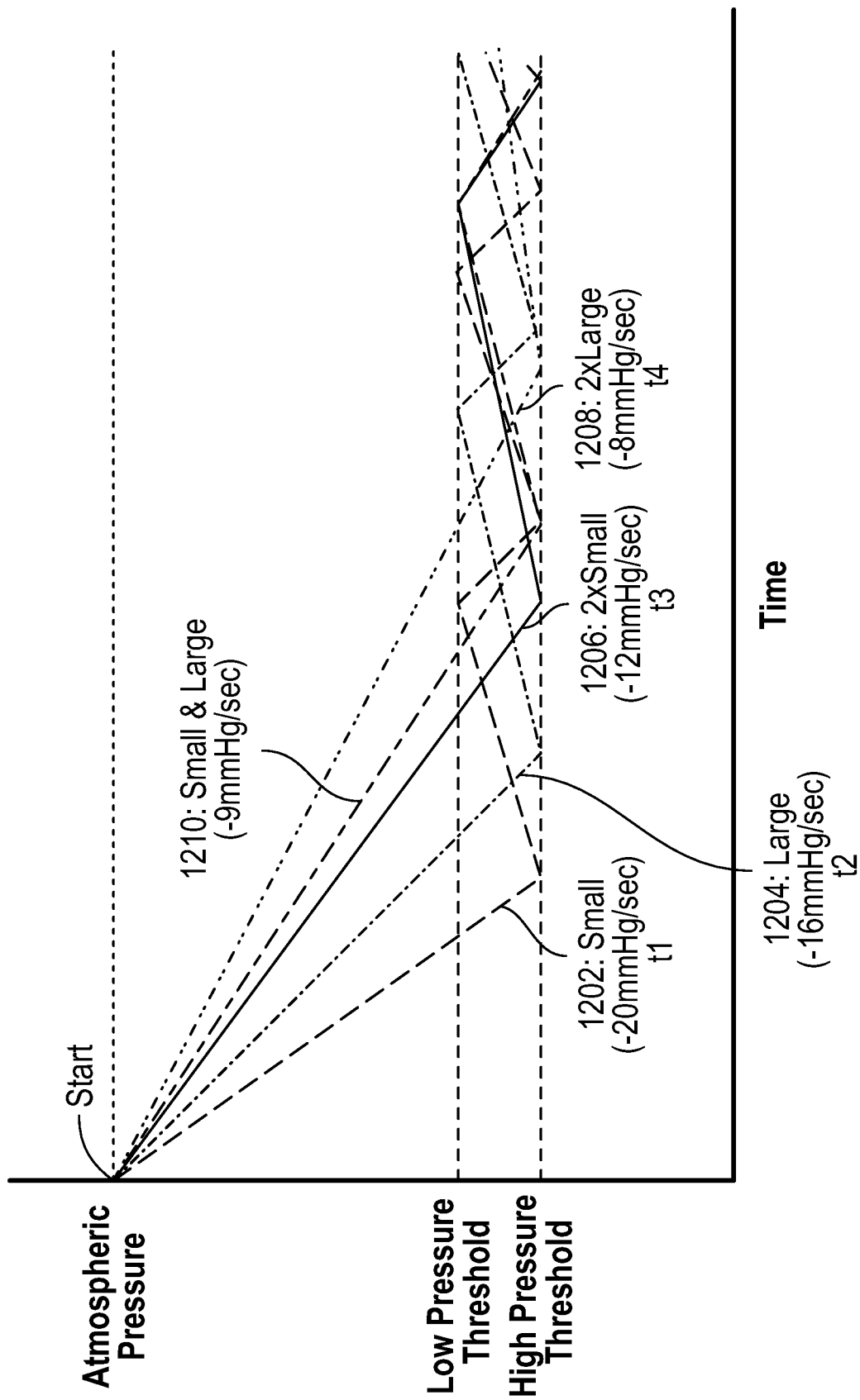
FIG. 12 illustrates pressure versus time graphs for different dressing sizes according to some embodiments.
Figure 13:
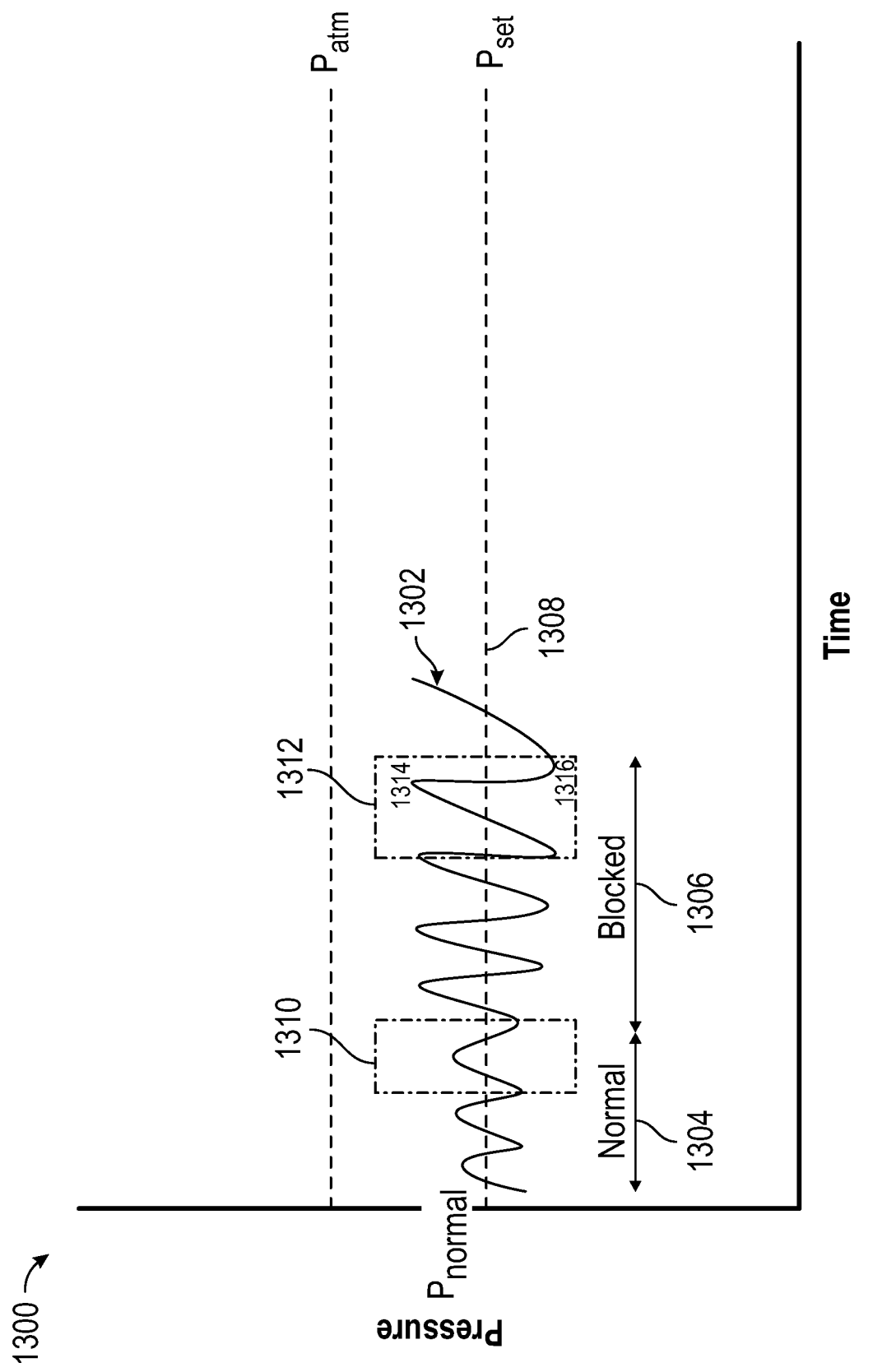
FIG. 13 illustrates a process for providing negative pressure wound therapy according to some embodiments.
Figure 15:
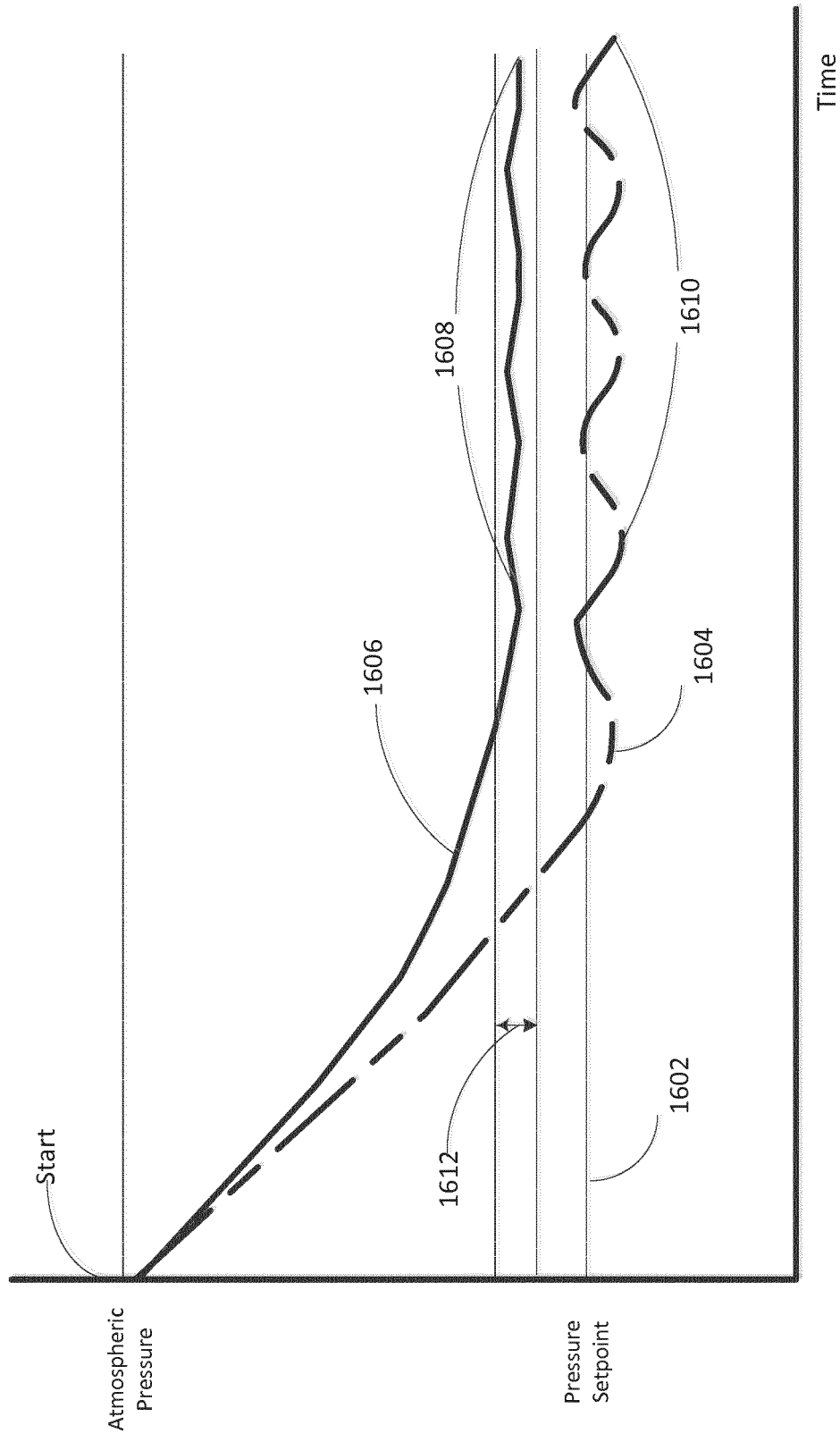
FIG. 15 illustrates pressure versus time graphs when a leak condition is detected according to some embodiments.

As described with respect to FIG. 12, some of the parameters or profiles can indicate sizes of one or more attached wound dressings. Additionally, the parameters or profiles can indicate blockage (FIGS. 13 and 14A-14D) or leak conditions (FIG. 15). In some embodiments, these conditions can be detected by the process 900 while the process in in block 908. Similarly, one or more condition detection can be disabled or enabled based on which of the blocks 902, 904, 906, or 908 the TNP system is currently operating in or is transitioning to.

Pump System Control

Figure 10:
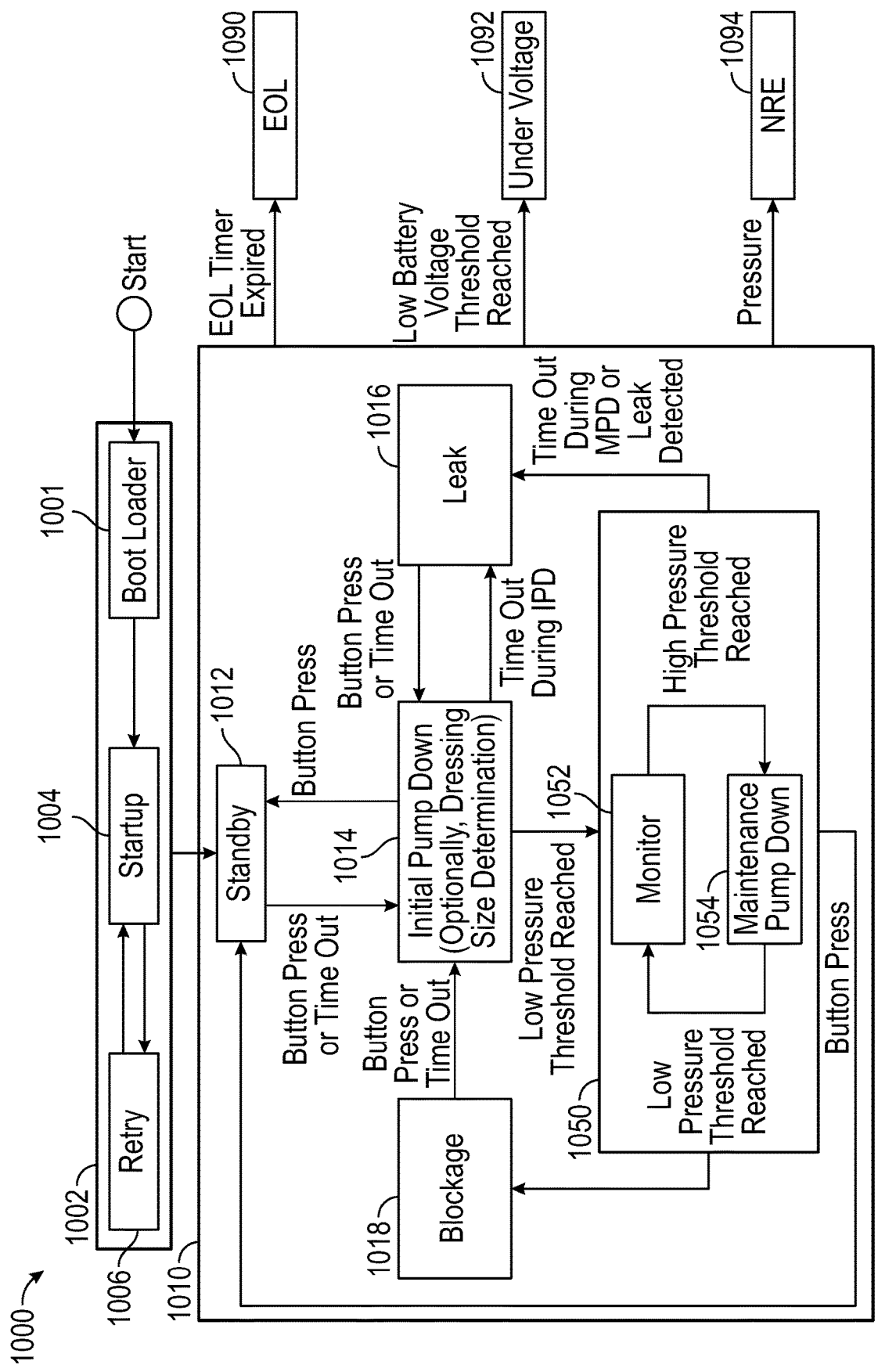
FIG. 10 illustrates a process for providing negative pressure wound therapy according to some embodiments.

FIG. 10 illustrates a process 1000 of operation of a TNP apparatus or pump system according to some embodiments, such as the system 511. The process 1000 can be executed by one or more processors as disclosed herein. For example, the process 1000 can provide a suitable balance between uninterrupted delivery of therapy or avoidance of inconveniencing the user by, for example, frequently or needlessly pausing or suspending therapy and a desire to conserve power, limit noise and vibration generated by the negative pressure source, etc. As is illustrated in FIG. 10, the operation of the pump system can, in some embodiments, be grouped into three general modes: initialization 1002, operational 1010, which includes maintenance 1050, and end of life 1090. As is illustrated in FIG. 10, categories 1002, 1010, and 1050 can each include multiple states and transitions between states.

In some embodiments, so long as a power source is not connected or removed, or the pump system has not been activated (for example, by pulling an activation strip, triggering a switch or button, or the like), the pump system can remain in an inactive state. While remaining in this state, the pump system can remain inactive. When the power source is connected or the pump system has been activated from the inactive state, such as being activated for the first time, the pump system can transition to an initialization mode 1002, where a bootloader 1001 can initiate a sequence of startup procedures as shown in block 1004. The bootloader 1001 can be stored on any suitable non-volatile memory such as, for example, read only memory (ROM), erasable programmable read only memory (EPROM), electrically erasable programmable read-only memory (EEPROM), and the like. In some embodiments, one or more processors can execute the bootloader 1001 upon startup. The startup procedures can include power on selftest(s) (POST) and other tests or procedures that can be performed as shown in startup block 1004. As shown in FIG. 10, the bootloader 1001 can initiate one or more of the POST(s) or one or more of the other tests. In some embodiments, the startup procedures can advantageously prepare or ensure that the pump system will deliver negative pressure wound therapy safely during operation.

Power on self-test(s) can include performing various checks to ensure proper functionality of the system, such as testing one or more components of the system including, but not limited to, memory such as memory 350 (for example, performing a check, such as a cyclic redundancy check (CRC check), of the program code to determine its integrity, testing the random access memory, etc.), reading the pressure sensor such as pressure sensors or monitors 397, to determine whether the pressure values are within suitable limits, reading the remaining capacity or life of the power source (for example, battery voltage, current, etc.) to determine whether it is within suitable limits, testing the negative pressure source, and the like. Other tests or procedures can include waiting for automatic test equipment (ATE), initializing a watch dog timer (WDT), checking whether the pump system has previously entered a non-recoverable error (NRE), and determining whether the pump system has reached the end of its allotted operational lifespan (also referred to as its end of life (EOL)), and the like. For example, in some embodiments, the WDT can advantageously be used as a countermeasure to a firmware execution hanging conditions, the check for a previous NRE can advantageously prevent the reuse of a device that has transitioned to an NRE state, and the check of whether the device has reached its end of life can advantageously prevent the reuse of a device that has transitioned to an EOL state.

In some embodiments, the bootloader 1001, which can be executed by the one or more processors, can also initiate the operational mode 1010. For example, as shown in FIG. 10, the bootloader can execute initialization of the operational mode 1010 after the initialization mode 1002 has been performed. In some embodiments, one or more indicators can indicate to the user (for example, by blinking or flashing once) that the pump system is undergoing POST test(s). In some embodiments, during the initialization mode 1002, all indicators can continuously remain on. In some cases, the one or more indicators can be one or more LEDs.

In some embodiments, the one or more indicators can blink or flash intermittently or continuously to indicate to the user that the system has passed the POST(s) or other tests and procedures. In some embodiments, one or more indicators positioned on external surface of the TNP device can include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "power source critical" indicator which can indicate that the power source is at or near a critical level. In some embodiments, the one or more indicators can be individually or cooperatively illuminated to indicate to the user that the pump system has passed POST(s) or other tests and procedures. For example, in some embodiments, the one or more indicators can be cooperatively illuminated to indicate that the system has passed the one or more tests such that the "OK" LED flashes once, the "leak" LED flashes once, the "dressing full" LED flashes once, and the "power source critical" LED flashes once. Similarly, if a previous non-recoverable error is discovered during startup or subsequently encountered during pump operation, the one or more indicators can be cooperatively illuminated such that the "OK" LED is solid, the "leak" LED is solid, the "dressing full" LED is solid, and the "power source critical" LED is solid. Any suitable individual or cooperative LED arrangement is envisioned in certain embodiments. In various embodiments, in addition to or instead of providing the visual indication using the one or more indicators, other indications can be provided, including audible, tactile, and the like.

In some embodiments, if one or more of the POST test(s) or other tests or procedures fail, the pump system can transition to a retry state 1006. The retry state 1006 can include a delay or require user input before retrying the POST test(s) or other tests or procedures. In some embodiments, the retry state 1006 can be executed until each test or procedure that is part of the initialization mode passes or otherwise does not fail. In some embodiments, if one or more of POST test(s) fail after one or more retries, the pump system can transition to a non-recoverable error state. While in this state, the pump system can deactivate therapy, and indicators can indicate to the user that an error was encountered. In some embodiments, all indicators can remain active. Based on the severity of error, in some embodiments, the pump system can recover from the error and continue operation (or transition to the non-recoverable error state 1094). As is illustrated, the pump system can transition to the non-recoverable error state 1094 upon encountering a fatal error during operation. Fatal errors can include program memory errors, program code errors (for example, encountering an invalid variable value), controller operation errors (for example, watchdog timer expires without being reset by the controller), component failure.

With continued reference to FIG. 10, in some embodiments, when initialization has been successfully completed in state 1004, the pump system can transition to the operational mode 1010. This transition can be indicated to the user by deactivating or activating one or more indicators. In some embodiments, when the pump system transitions into the operational mode 1010, the pump system can first enter a standby or paused state 1012. While the pump system remains in the standby state 1012, the user can be provided an indication, such as by deactivating or activating indicators (for example, an OK indicator or a dressing indicator). In some embodiments, the user can be provided an indication of the standby state 1012 by deactivating all indicators. In some embodiments, therapy can be suspended while the pump system remains in the standby state 1012. For example, the source of negative pressure such as sources of negative pressure 1010, 1019, 1218, can be deactivated (or turned off). In some embodiments, indication can be provided to the user by deactivating the source of negative pressure.

In some embodiments, the pump system can be configured to make a transition from the standby state 1012 to an initial pump down ("IPD") state 1014 (where the pump system is configured to deliver therapy) in response to receiving a signal from the user. For example, the user can press a button (see FIG. 2 (illustrating 212*b*) or 5) to start, suspend, or restart therapy. In some embodiments, the pump system can monitor the duration of time the pump system remains in the standby state 1012. This can be accomplished, for example, by maintaining a timer (in firmware, software, hardware or any combination thereof), which can be reset and started when the pump system transitions into the standby state 1012. The pump system can automatically make the transition from the standby state 1012 to the IPD state 1014 when the time duration exceeds a threshold (for example, times out). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained below), the threshold can be decreased used over the lifespan of the pump system. This can advantageously ensure that a power source, such as one or more batteries, is used more efficiently over the lifespan of the pump system by reducing the amount of time spent in the standby state 1012 and utilizing more of the power source by activating the pump sooner. In some embodiments, the pump system can monitor the entire amount of time spent in the standby state and store this information in memory.

During the IPD state 1014, the pump system can activate the source of negative pressure to begin therapy and reduce pressure in the system or some portion thereof, such as a fluid flow path between a source of negative pressure and a wound dressing. In some embodiments, the pump system can reduce pressure in the system to a desired pressure, such as a low pressure setpoint or threshold. The pump system can intermittently or continuously monitor the pressure in the pump system or some portion thereof. For example, the pump system can monitor the pressure in the pump system or some portion thereof at a preset sampling rate of approximately 100 ms. In some embodiments, the sampling rate can be between approximately 20 ms and approximately 500 ms, between approximately 50 ms and 250 ms, between approximately 80 ms and 150 ms, approximately 100 ms, any value or subrange with these ranges, or any other sampling rate as desired. In some embodiments, the pump system can also calculate the rate of pressure change to estimate the amount of time until the pump system reaches a desired pressure, such as the low pressure threshold. In some cases, as described herein, the pump system can determine in the IPD state 1014 sizes of one or more dressings connected to the pump system.

In some embodiments, one or more indicators can blink or flash intermittently or continuously to indicate to the user that the pump system is in the IPD state. For example in some embodiments, the one or more indicators can include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity (or "canister full" indicator which can indicated that a canister is at or near capacity), and a "power source critical" indicator which can indicate that the power source capacity is at or near a critical level. In some embodiments, the one or more indicators can be individually or cooperatively illuminated to indicate to the user that the system is in the IPD state. For example, in some embodiments, the one or more indicators can be cooperatively illuminated to indicate that the system is in the IPD state such that the "OK" LED is flashing, the "leak" LED is flashing, the "dressing full" LED is off, and the "power source critical" LED does not change (on, off, or flashing). Any suitable individual or cooperative LED arrangement is envisioned in certain embodiments. Once a desired negative pressure setpoint is reached during the IPD state, the one or more indicators can be individually or cooperatively illuminated to indicate that the desired negative pressure has been reached. For example, in some embodiments, the one or more indicators can be cooperatively illuminated to indicate that the negative pressure has been reached such that the "OK" LED is flashing, the "leak" LED is off, the "dressing full" LED is off, and the "power source critical" LED does not change (on, off, or flashing). In some embodiments, this same illumination pattern can also be used to indicate that the pump system is functioning properly, such as during the IPD state to indicate that the pump system is functioning properly during the IPD state, in addition to flashing to indicate that the negative pressure has been reached during the IPD state. In various embodiments, in addition to or instead of providing the visual indication using the one or more indicators, other indications can be provided, including audible, tactile, and the like.

In some embodiments, the user can pause therapy by activating the switch (for example, pressing the button), thereby causing the pump system to make a transition from the IPD state 1014 to the standby state 1012. In some embodiments, the pump system can be configured so that the user can only pause therapy, whereas disconnecting the power source (for example, removing power source) stops therapy. As such, in some embodiments, the pump system can potentially time out while in the standby state 1012 and resume operation thereby reducing any energy expended while in the standby state 1012. After being paused by the user, the pump system can transition from the standby state 1012 to the IPD state 1014 upon receiving a user input such as a button press. In some embodiments, after being paused by the user, the pump system can automatically make the transition from the standby state 1012 to the IPD state 1014 when the time duration exceeds a threshold. The threshold can be the same or different than the threshold of the standby state 1012 described above when the pump system enters the standby state 1012 after startup 1004.

When the pump system transitions into and remains in the standby state 1012, the user can be provided an indication. For example, in some embodiments, all indicators can be deactivated. In some embodiments, the pump system can deactivate an indicator (for example, an OK indicator) and cause another indicator (for example, a dressing indicator) to flash or blink. In some embodiments, one or more indicators can blink or flash intermittently or continuously to indicate to the user that the system is in the standby state. For example, in some embodiments, the one or more indicators can include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "power source critical" indicator which can indicate that the power source capacity is at or near a critical level. In some embodiments, the one or more indicators can be individually or cooperatively illuminated to indicate to the user that the system is in the standby state. For example, in some embodiments, the one or more indicators can be cooperatively illuminated to indicate that the system is in the standby state such that the "OK" LED is off, the "leak" LED is off, the "dressing full" LED is off, and the "power source critical" LED is off. In some embodiments, this same illumination pattern can also be used to indicate that the pump system has completed its course of negative pressure wound therapy or to indicate that the power source, such as one or more batteries, has been depleted, in addition to indicating that the pump is in the standby state. Any suitable cooperative LED arrangement is envisioned in certain embodiments. In various embodiments, in addition to or instead of providing the visual indication using the one or more indicators, other indications can be provided, including audible, tactile, and the like. In some embodiments, therapy can be suspended while the pump system remains in the standby state 1012. For example, the source of negative pressure can be deactivated (or turned off), which provides the indication to the user that the pump system is in the standby state 1012. Similarly, the pump system can indicate various current operating states or transition into states with the one or more indicators.

With continued reference to FIG. 10, in some embodiments, the pump system can transition from the initial pump down state 1014 into a leak state 1016 when a number of retry cycles exceeds a retry limit or when a duty cycle of the pump (explained below) is determined to exceed a duty cycle limit. In some embodiments, exceeding a retry limit or duty cycle limit can reflect the presence of a leak in the system. In some embodiments, the pump system can transition from the IPD state 1014 to the leak state 1016 when a threshold pressure is not reached within a desired amount of time. The inability for the threshold pressure to reach the threshold pressure within a desired amount of time can reflect the presence of a leak in the system. Additionally or alternatively, in some embodiments, an indicator (for example, a leak indicator or dressing indicator) can blink or flash intermittently or continuously to indicate to the user the presence of a leak in the system. In some embodiments, one or more indicators can blink or flash intermittently or continuously to indicate to the user the presence of a leak.

After entering the leak state 1016, the pump system can transition from the leak state 1016 to the IPD state 1014 upon receiving a user input such as a button press. This can advantageously give the user some time to mitigate or remove the leak, such as by checking the connections of the wound dressing or checking the seal of the wound dressing around the wound. In some embodiments, the pump system can monitor the duration of time the pump system remains in the leak state 1016. This can be accomplished, for example, by maintaining a timer (in firmware, software, hardware or any combination thereof), which can be reset and started when the pump system transitions into the leak state 1016. In some embodiments, after entering the leak state 1016, the pump system can automatically make the transition from the leak state 1016 to the IPD state 1014 when the time duration exceeds a threshold. The threshold can be the same or different than the other time thresholds described herein, such as that of the standby state 1012 to the IPD state 1014. The threshold can be the same or different depending on the state or mode prior to transitioning to the leak state 1016 (for example, the IPD state 1014 or the maintenance mode 1050). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained below), the threshold can be decreased provided the power source has sufficient capacity remaining. This can advantageously ensure that the power source is more efficiently used over the lifespan of the pump system by reducing the amount of time spent in the leak state 1016 and utilizing more of the power source by activating the pump sooner. The pump system can transition into other modes or states, such as the maintenance mode 1050, after activating the switch or automatically after exceeding the threshold. In some embodiments, the pump system can transition to the IPD state 1014 or the maintenance mode 1050 depending on operating conditions, such as the pressure at the time of the transition.

As noted above, in some embodiments, the pump system can be configured to operate in a canisterless system, in which the wound dressing retains exudate aspirated from the wound. Such dressing can include a filter, such as a hydrophobic filter, that prevents passage of liquids downstream of the dressing (toward the pump system). In other embodiments, the pump system can be configured to operate in system having a canister for storing at least part of exudate aspirated from the wound. Such canister can include a filter, such as a hydrophobic filter, that prevents passage of liquids downstream of the dressing (toward the pump system). In yet other embodiments, both the dressing and the canister can include filters that prevent passage of liquids downstream of the dressing and the canister.

With continued reference to FIG. 10, in some embodiments, the pump system can be configured to transition from the initial pump down state 1014 into a blockage state 1018, which can be associated with dressing filter blocked or canister full state, when the system determines that the filter, such as a wound dressing filter, has been blocked (for example, caused by the wound dressing being filled with exudate to capacity or nearly to capacity) or canister is full or substantially full, which can cause a canister filter to be blocked as described herein. In some embodiments, an indicator (for example, a filter blocked or canister full indicator) can blink or flash intermittently or continuously to indicate to the user the presence of a blockage. In some embodiments, one or more indicators can blink or flash intermittently or continuously to indicate to the user the presence of a blockage. Further details on filter block or canister full detection are disclosed in connection with FIGS. 13, 14A-14D, and 15.

After entering the filter blocked or canister full state 1018, the pump system can transition from the state 1018 to the IPD state 1014 upon receiving a user input, such as a button press. This can advantageously give the user an opportunity to mitigate or remove the blockage, such as by changing the wound dressing (or the canister). In some embodiments, the pump system can monitor the duration of time the pump system remains in blockage state 1018. This can be accomplished, for example, by maintaining a timer (in firmware, software, hardware or any combination thereof), which can be reset and started when the pump system transitions into blockage state 1018. In some embodiments, after entering the state 1018, the pump system can automatically make the transition from the state 1018 to the IPD state 1014 when the time duration exceeds a threshold. The threshold can be the same or different than the other time thresholds described herein, such as that of the standby state 1012 to the IPD state 1014 or the leak state 1016 to the IPD state 1014. The threshold can be the same or different depending on the state or mode prior to transitioning to the blockage state 1018 (for example, the IPD state 1014 or the maintenance mode 1050). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained herein), the threshold can be decreased provided the power source has sufficient capacity remaining. This can advantageously ensure that the power source is more efficiently used over the lifespan of the pump system by reducing the amount of time spent in the blockage state 1018 and utilizing more of the power source by activating the pump sooner. The pump system can transition into other modes or states, such as the maintenance mode 1050, after activating the switch or automatically after exceeding the threshold. In some embodiments, the pump system can transition to the IPD state 1014 or the maintenance mode 1050 depending on operating conditions, such as the pressure at the time of the transition.

With continued reference to FIG. 10, in some embodiments, during the IPD state 1014, once the pump system has detected that the pressure within the pump system or some portion thereof, such as a fluid flow path between a source of negative pressure and a wound dressing, is at or around the low pressure threshold, the pump system can transition into a maintenance mode 1050 and, in particular, to the monitor state 1052. For example, the low pressure threshold can be approximately −90 mmHg. In some embodiments, the low pressure threshold can be between approximately −50 mmHg and approximately −250 mmHg, between approximately −105 mmHg and approximately −125 mmHg, between approximately −80 mmHg and −105 mmHg, approximately −94 mmHg, any value or subrange within these ranges, or any other value as desired. As described with respect to FIG. 12, in some embodiments, one or more sizes of the one or more attached wound dressings can be determined in block 1014 based on the amount of time for the initial pump down, calculated rate of pressure change during the transition from the IPD state 1014 to the maintenance mode 1050, or the like.

During the maintenance mode 1050, the pump system can advantageously monitor and maintain the pressure within the pump system or some portion thereof, such as a fluid flow path between a source of negative pressure and a wound dressing, within a target pressure range (or operating range). For example, in some embodiments, during the maintenance mode 1050, the pump system can maintain the pump system or some portion thereof between a high pressure threshold and a low pressure threshold. For example, the high pressure threshold can be approximately −70 mmHg. In some embodiments, the high pressure threshold can be between approximately −40 mmHg and approximately −200 mmHg, between approximately −60 mmHg and approximately −100 mmHg, between approximately −70 mmHg and −80 mmHg, approximately −71 mmHg, approximately −67 mmHg, any value or subrange within these ranges, or any other value as desired. The low pressure threshold can be approximately −90 mmHg. In some embodiments, the low pressure threshold during the maintenance mode 1050 can be the same as the low pressure threshold during the IPD state 1014. In some embodiments, the low pressure threshold during the maintenance mode 1050 can be different from the low pressure threshold during the IPD state 1014. As shown in the illustrated embodiment, the maintenance mode 1050 can include a monitor state 1052 and a maintenance pump down ("MPD") state 1054.

In some embodiments, one or more indicators can blink or flash intermittently or continuously to indicate to the user that the system is in the MPD state. During the monitor state 1052, the pump system can monitor the pressure in the pump system or some portion thereof, such as a fluid flow path between a source of negative pressure and a wound dressing, to ensure that the pressure within the pump system or the monitored portion thereof is maintained between a high pressure threshold and a low pressure threshold. The source of negative pressure can be deactivated during the monitor state 1052. The pump system can intermittently or continuously monitor the pressure in the pump system or some portion thereof. For example, the pump system can monitor the pressure in the pump system or some portion thereof at a preset sampling rate of approximately 1 second. In some embodiments, the sampling rate can be between approximately 50 ms and approximately 5 seconds, between approximately 200 ms and 2 seconds, between approximately 500 ms and 2 seconds, approximately 1 second, any value or subrange with these ranges, or any other sampling rate as desired. In some embodiments, the sampling rate during the monitor state 1052 can be less than the sampling rate during the IPD state 1014 to advantageously reduce power usage and extend the life of the power source. A lower sampling rate can be used in some embodiments as the rate of pressure change during the monitor state 1052 (for example, when the source of negative pressure is deactivated) can be less than the rate of pressure change when the source of negative pressure is activated. In some embodiments, the pump system can also calculate the rate of pressure change to estimate the amount of time until the pump system reaches a desired pressure, such as a low pressure threshold.

In some embodiments, one or more indicators can blink or flash intermittently or continuously to indicate to the user that the system is in the monitor state. The pump system can stay in the monitor state 1052 until the pump system detects that the pressure in the pump system or some portion thereof, such as a fluid flow path between a source of negative pressure and a wound dressing, is at or around a high pressure threshold. Upon detecting that the pump system or some portion thereof is at or around the high pressure threshold, the pump system can transition to the MPD state 1054. During the MPD state 1054, the pump system can activate the source of negative pressure to begin therapy and reduce pressure in the system or some portion thereof until the pressure is at or near the low pressure threshold. In some embodiments, the low pressure threshold can be the same or similar to the low pressure threshold discussed in connection with the IPD state 1014. In some embodiments, the low pressure threshold can be different from that in the IPD state 1014.

The pump system can continually monitor the pressure in the pump system at a preset sampling rate. In some embodiments, the sampling rate can be the same or similar to the low pressure threshold discussed in connection with the IPD state 1014. In some embodiments, the sampling rate can be different from the sampling rate during the IPD state 1014. In some embodiments, the pump system can also calculate the rate of pressure change to estimate the amount of time until the pump system reaches a desired pressure, such as the low pressure threshold. When the pump system detects that the pressure in the pump system or some portion thereof is at or around the low pressure threshold, the pump system can transition back to the monitor state 1052.

With reference to FIG. 10, in some embodiments, the user can pause therapy by activating the switch (for example, pressing the button), thereby causing the pump system to make a transition from the maintenance mode 1050 to the standby state 1012. After being paused by the user, the pump system can transition from the standby state 1012 to the IPD state 1014 upon receiving a user input such as a button press. In some embodiments, after being paused by the user, the pump system can automatically make the transition from the standby state 1012 to the IPD state 1014 when the time duration exceeds a threshold. The threshold can be the same or different than the thresholds discussed above, such as the threshold when the pump system enters the standby state 1012 from the IPD state 1014 from a button press. In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained below), the threshold can be decreased provided the power source has sufficient capacity remaining. In some embodiments, the pump system can transition into the maintenance mode 1050 after activating the switch or automatically after exceeding the threshold. In some embodiments, the pump system can transition to the IPD state 1014 or the maintenance mode 1050 depending on operating conditions, such as the pressure at the time of the transition.

When the pump system transitions into and remains in the standby state 1012, the user can be provided an indication. For example, in some embodiments, all indicators can be deactivated. In some embodiments, the pump system can deactivate an indicator (for example, an OK indicator) and cause another indicator (for example, a dressing indicator) to flash or blink. In some embodiments, therapy can be suspended while the pump system remains in the standby state 1012. For example, the source of negative pressure can be deactivated (or turned off), which provides the indication to the user that the pump system is in the standby state 1012.

With continued reference to FIG. 10, in some embodiments, the pump system can transition from the maintenance mode 1050 into a leak state 1016 when a threshold pressure is not reached within a desired amount of time. The inability for the threshold pressure to reach the threshold pressure within a desired amount of time can reflect the presence of a leak in the system. In some embodiments, the pump system can transition from the maintenance mode 1050 to the leak state 1016 when a number of retry cycles exceeds a retry limit or when the duty cycle of the pump is determined to exceed a duty cycle limit. In some embodiments, exceeding a retry limit or duty cycle limit can reflect the presence of a leak in the system. Additionally, as will be described in further detail with respect to FIG. 15, the pump system may transition into the leak state 1016 when the pump system detects peak-to-trough pressure measurements to be below a threshold for a period of time. In some embodiments, an indicator (for example, a leak indicator or dressing indicator) can blink or flash intermittently or continuously to indicate to the user the presence of a leak in the system.

With continued reference to FIG. 10, in some embodiments, the pump system can be configured to transition from the maintenance mode 1050 into the blockage state 1018 when the system determines that the filter, such as the wound dressing filter (or the canister filter), has been blocked (for example, caused by the wound dressing or canister being filled with exudate to capacity or nearly to capacity). In some embodiments, an indicator (for example, a filter blocked indicator) can blink or flash intermittently or continuously to indicate to the user the presence of a blockage.

With continued reference to FIG. 10, in some embodiments, the pump system can be configured to monitor the remaining capacity or life of the power source (for example, by periodically reading or sampling the power source voltage, current, etc.). The pump system can be configured to indicate to the user the remaining capacity. For example, if the power source is determined to have a normal remaining capacity (for example, as a result of comparison to a threshold, such as 2.7V, 2.6V, 2.5V, etc.), an indicator (for example, a power source indicator) can be deactivated. If the power source is determined to have low remaining capacity, the pump system, can provide an indication to the user by, for example, causing an indicator (for example, a power source indicator) to blink or flash. In some embodiments, an indicator (for example, a power source indicator) can be configured to be blinking or flashing intermittently or continuously regardless of the state the pump system is in or only in particular states.

In some embodiments, when the remaining capacity of the power source is determined to be at or near a critical level (for example, as a result of comparison to a threshold, such as 2.4V, 2.3V, 2.2V, etc.), the pump system can transition into an under voltage or power source critical state 1092. In some embodiments, the pump system can remain in this state until the capacity of the power source is increased, such as by replacing or recharging the power source. The pump system can deactivate therapy while remaining in the power source critical state 1092. In addition, the pump system can be configured to indicate to the user that the power source is at or near the critical level by, for example, deactivating all indicators. In some embodiments, when the pause/resume button is pressed after the pump system has transitioned to the under voltage state 1092, the pump system can be configured to indicate that the device has not yet reached its end of life (EOL) by, for example, flashing a power source indicator LED.

With continued reference to FIG. 10, in some embodiments, the pump system can be configured to provide therapy for a predetermined period of time, such as approximately 1 day, 2-10 days, up to 30 days, etc. following a first activation. In some embodiments, such period of time can be a preset value, changed by the user, or varied based on various operating conditions or on any combination thereof. The pump system can be disposed upon the expiration of such period of time. Once the pump system has been activated, the pump system can monitor the duration it has remained active. In some embodiments, the pump system can monitor the cumulative duration the system has remained active. This can be accomplished, for example, by maintaining a timer (in firmware, software, hardware or any combination thereof), that reflects such duration.

When the duration reaches or exceeds a threshold (for example, 10 days), the pump system can transition to an end of life (EOL) state 1090. The pump system can deactivate therapy while remaining in state 1090 and to indicate to the user that the end of the pump system's usable life has been reached. For example, the pump system can deactivate all indicators or deactivate the button. In some embodiments, when the pump system is disposable, transitioning to the end of life state 1090 means that the pump system can be disposed of. The pump system can disable reactivation of the pump system once the end of life has been reached. For example, the pump system can be configured to not allow reactivation even if the power source is disconnected and reconnected later, which can be accomplished by storing an indication, value, flag, etc. in the read only memory.

In some embodiments, the pressure during the IPD or MPD state can be sampled after a preset period of time as elapsed from when the IPD or MPD state was initiated. After this time period elapses, the pressure can be sampled in consecutive samples, and two or more of the consecutive samples can be averaged. In some embodiments, sampling of the pressure can be synchronized with the drive signal. For example, sampling of the pressure within the pump system or some portion thereof, such as a fluid flow path between a source of negative pressure and a wound dressing, can be performed when the drive signal is approximately at an amplitude that is substantially at an offset (explained below) or at a zero value. In some embodiments, two or more groups of consecutive pressure samples can be averaged to minimize measurement errors due to pressure fluctuations caused by operation of the motor. In some embodiments, averaging two or more groups of consecutive pressure samples can compensate for the time needed to detect the zero value when the pressure samples are synchronized at a zero value. Movement of the pump assembly can highly influence pressure within the pump system, such as a manifold of the pump system. By synchronizing sampling of the pressure with the offset or zero value of the drive signal, any measurement errors due to pressure fluctuations caused by operation of the motor can be reduced. In some embodiments, sampling of the pressure can be synchronized with the local maxima or local minima of the drive signal. In some embodiments, sampling of the pressure can be synchronized with certain portions of the drive signal, such as portions of the drive signal with a negative rate of change or a positive rate of change.

In some embodiments, the pressure can be sampled one or more times at or around the one or more selected sampling amplitudes such as the offset or zero value, local maxima, or local minima. This can beneficially reduce the likelihood of sampling errors and compensate for the delay elapsed between detection of the one or more selected sampling amplitudes and sampling of the pressure. For example, in some embodiments, the pump system can take 8 consecutive samples at approximately each offset or zero value. Accordingly, the pump system can take 16 samples over a single period of the drive signal. In some embodiments, the pump system can average some or all of the samples taken over a period.

FIG. 11 illustrates a graph 1100 of pressure versus time according to some embodiments. Graph 1100 illustrates pressure changes during the IPD state 1110, monitor state 1120, and MPD state 1130, one or more of which can correspond to states 1014, 1052, and 1054 in FIG. 10. As shown in graph 1100, during the IPD state 1110, the pump system can sample the pressure at two or more points in time represented on the graph as points 1112, 1114 corresponding to pressures P1 at time t1 and P2 at time t2 respectively. The rate of change of pressure between these two points can be calculated according to: $(P2-P1)/(t2-t1)$.

In some circumstances, an abrupt pressure drop, for example from point 1112 to point 1114, is indicative of a transient blockage, such as a kinked conduit in the fluid flow path, dressing full, canister full, or the like. As described herein, the pump system can detect such blockage condition by determining that the rate of change of pressure exceeds a threshold.

Dressing Capacity or Size Determination

In some embodiments, such as in a multiple dressing TNP system or pump assembly, capacity(ies) or size(s) of one or more dressings, such as one or more dressings 700, can be determined by one or more processors. In some cases, dressing size(s) can be determined based on determining the amount of time for initial pump down (such as, in IPD 1014 state) or reaching the negative pressure setpoint after therapy is initiated. For example, achieving the negative pressure setpoint in a system with a large dressing will take longer than in a system with a small dressing. For example, as illustrated in FIG. 12, a small dressing pressure profile 1202 is associated with IPD of t1, while a large dressing pressure profile 1204 is associated with IPD of t2. Since the time required to pump down a smaller volume for a given pump is shorter, t1 is smaller than t2. As explained herein, in some cases, the TNP system can use a look up table that associates IPD time to dressing sizes to determine the dressing size(s). As described herein, the pump system can determine sizes for combinations of two or more wound dressings.

When multiple dressings are present, multiple pressure sensors can be used to monitor pressure in multiple fluid flowpaths or a single pressure sensor can be used to measure combined pressure in the multiple fluid flowpaths. In some cases, dressing size(s) can be determined in based on time to reestablish the negative pressure setpoint (such as, MPD state 1054).

Additionally or alternatively, in some cases, the TNP system can determine sizes of one or more wound dressings based on a rate of pressure change. The rate of pressure change can be measured as differential change between two pressures known at two times divided by the differential of the corresponding two times (for example, $(P2-P1)/(t2-t1)$ as disclosed herein). As described herein, a large wound dressing includes more volume than a small wound dressing. Thus, when measuring the rate of pressure change, the large wound dressing would exhibit smaller rate of pressure change than the small wound dressing. Since the volume of a given wound dressing can be obtained beforehand from a manufacturer, associated pressure change can be determined during calibration and used during provision of therapy. For example, a look up table associating a rate of pressure change with wound dressing sizes can be stored in memory of the TNP system. Alternatively or additionally, a manufacturer can measure the volume of manufactured wound dressings and provide the volume measurement along with the wound dressing with which a similar look up table can associate a detected rate of pressure change and identify wound dressing size.

FIG. 12 illustrates, for a given pump having a known aspirating capacity, a rate of pressure change determined when aspirating fluid with the pump using a small wound dressing will be larger in magnitude than if a larger wound dressing was used (for example, compare pressure change of −20 mmHg/sec 1202 with a small dressing with pressure change of −16 mmHg/sec 1204 with the larger dressing). Based on the rate of pressure change, the TNP system, for instance, via one or more processors, can determine a size of a coupled wound dressing.

In some embodiments, the TNP system may use a look up table for associating detected rate of pressure change with one or more known sizes of different wound dressings. For example, as FIG. 12 illustrates, a rate of pressure change of −20 mmHg/sec can be associated with a small wound dressing, while a rate of pressure change of −16 mmHg/sec may be associated with a large wound dressing. Using the look up table, the TNP system may determine which wound dressing is currently coupled with the system.

As illustrated with FIGS. 4A-4B and 5, a TNP system may be concurrently coupled with more than one wound dressings in a configuration where one negative pressure source can provide negative pressure to multiple wound dressings. In some embodiments, for a given size wound dressing, having another wound dressing of similar size (for example, two small wound dressings or two large wound dressings) can manifest a rate of pressure change that is approximately half in magnitude to a single wound dressing (for example, compare 1202 to 1206 or 1204 to 1208 in FIG. 12).

In some cases, using the look up tables which can include associations with such multiple wound dressing configurations, or identifying a configuration that would best match a measured rate of pressure change with a combination of a plurality of known size wound dressings and their associated rates of pressure change, the TNP system may determine sizes of multiple coupled wound dressings. In some embodiments, where two different size wound dressings are coupled to the TNP system (for example, small and large 1210 in FIG. 12), the TNP system may associate the determined rate of change with a combination of known wound dressing sizes.

In some embodiments, detecting the rate of pressure change during the initial pump down can provide high degree of confidence of the detected rate of pressure change. Since detection of the wound dressing sizes is preferably performed at the start of the therapy and may not need to be redetermined unless the wound dressings are switched out, entire or partial duration of initial pump down can be advantageous for detecting wound dressing sizes. However, as described herein, in some embodiments detecting the rate of pressure change can be performed over a shorter time frame (for example, at times between t1 time 1112 and t2 time 1114 in FIG. 11).

Blockage Detection

In some embodiments, a TNP system or pump assembly can detect and provide indication of a blockage, which can include canister pre-full or full, dressing pre-full or full, or other type of blockage in one or more fluid flow paths. As explained herein, for example, this determination can be made in when the process 900 of FIG. 9 is in standby state (block 908). As another example, this determination can be made when the process 1000 of FIG. 10 is in the maintenance mode states (block 1050). During operation, the pump generates pressure pulses or signals that are propagated through the fluid flow path(s). The pressure signals, which can be detected by one or more pressure sensors, are illustrated by the pressure curve 1302 of FIG. 13 according to some embodiments. As is illustrated in region 1304, pressure in a fluid flow path varies or oscillates around a particular negative pressure setpoint 1308 during normal operation of the system. Magnitude of pressure variation can be inversely proportional to the volume of the fluid flow path. Region 1306 illustrates pressure pulses in the flow path in presence of a blockage. Such blockage may be caused by, for example, the canister or dressing becoming full or a canister or dressing filter becoming occluded or blocked.

As is illustrated in region 1306, presence of a blockage causes a reduced volume to be seen upstream of the canister or dressing, and the amplitude of the pressure pulses changes (for example, increases). The frequency of a pressure signal can also change (for example, slows down or decreases). These changes in the one or more parameters of the pressure signal can be caused by the pump evacuating fluid from a reduced volume in the fluid flow path, with the reduction being due to the blockage. Observed changes in one or more parameters of the pressure signal can be used to identify the type of blockage present, such as distinguish between canister full, dressing full, or other types of blockages in the fluid flow path. The observed in the one or more parameters of the pressure signal can additionally or alternatively be used to identify remaining capacity of one or more wound dressings in a multiple dressing system, such as the one illustrated in FIGS. 4A-4B and 5. Changes in the amplitude or frequency of the pressure signal can be measured using a variety of techniques, such as by measuring peak-to-trough change (for example, peak 1314 to trough 1316).

In some cases, peak-to-trough value(s) for detecting blockage in one or more fluid flow paths can be measured after the pump system reaches the negative pressure setpoint 1308 (such as, for example in the steady state 908). Before reaching the pressure setpoint 1308, too much fluid may be evacuated by the TNP system to provide meaningful peak-to-trough measurements. Before reaching the negative pressure setpoint, peak-to-trough measurements may be too small to meaningfully determine presence of a blockage condition.

In certain embodiments, the changes in the pressure pulse signal can be magnified or enhanced by varying the pump speed, varying the cadence of the pump, such as by adjusting PWM parameters, turning the pump off and on, or the like. Such adjustments of pump operation are not required but can be performed over short time duration and the changes can be small such that the operation of the system remains relatively unaffected.

Blockage condition can be detected by collecting a one or more pressure sensor readings. For example, a single pressure sensor can be used to determine pressure in one or more fluid flow paths. One or more processors (as described herein) can use the one or more pressure sensor readings to determine one or more peak-to-trough values and compare the determined value(s) to one or more thresholds. The one or more thresholds can be determined or selected based on dressing sizes in a multiple dressing system, which can be detected as described herein. The one or more thresholds can be associated with expected pressure variations during normal operation, such as in the region 1304 of FIG. 13. For example, in a two dressing system, the combined volume of two small dressings can correspond to a threshold of T1, while the combined volume of two large dressings can correspond to a threshold of T2. T2 can be smaller than T1 because the combined volume of two large dressings is greater than the combined volume of two small dressings. The processor can compare determine peak-to-trough value(s) to the particular threshold (corresponding to the detected dressing sizes) and indicate presence of blockage if the threshold is satisfied (such as, exceeded as illustrated in the region 1306 of FIG. 13).

In some cases, one or more thresholds can be determined or selected to permit detection of a dressing pre-full condition. For example, a threshold can be determined to detect and alert a user to at least one of the dressings in a multiple dressing system being 50% full, 75% full, or the like. This can be advantageous to filling of at least one of the dressings with wound fluid to capacity and resulting blockage of the dressing filter, which can lead to adverse effects including, but not limited to one or more of, pooling of exudate, infection, or maceration.

In some cases, peak-to-trough measurement can be performed over a time duration (for example, 2 seconds or any other suitable duration which may be vary between sample periods). A number of readings of the plurality of readings, such as 25 sample periods out of 30 or any other suitable number, can be checked to determine if each indicates that the a blockage is present. If it is determined that the peak-to-trough pressure for a particular sample period satisfies the threshold, then the particular sample period indicates that the blockage is present.

One or more thresholds can additionally or alternatively can be determined based on the negative pressure setpoint. For example, a greater negative pressure setpoint can be associated with a greater expected variation of pressure and a higher threshold as compared to a smaller negative pressure setpoint.

Blockage determination can be performed on a sliding window basis. For example, a sliding window of 25 out of 30 sample periods can be analyzed and if 25 sample periods are determined to indicate blockage, blockage can be indicated. Assuming that, for example, the sample period is 2 seconds, using a sliding window of 25 out of 30 sample periods effectively results in determining whether change in pressure pulse amplitude exceeds the threshold for 60 seconds. This can prevent generation of unnecessary or undesirable blockage alarms.

Alternatively or additionally, blockage can be detected if a single sample period indicates blockage. However, using a plurality of sample periods can mitigate the effects of one or more transient conditions in the fluid flow path or one or more errant pressure readings. Alternatively or additionally, blockage detection can be performed by measuring the frequency of detected pressure signal and comparing the measured frequency to one or more suitable thresholds.

As described herein, multiple pressure sensors can be placed in the fluid flow path to facilitate detection of one or more of the above-described conditions. For example, in addition to or instead of the pressure sensor being placed in the pump inlet, a pressure sensor can be placed in the wound or under the dressing to directly determine the wound pressure. Measuring pressure at different locations in the fluid flow path, such as in the canister and at the wound, can facilitate detection of blockages, leaks, or the like.

FIGS. 14A-14D illustrate graphs of pressure signals according to some embodiments. Curve 1402A can correspond to a signal observed when the canister and/or one or more dressings are relatively empty. For example, a canister may be configured to hold up to 750 mL fluid volume, and curve 1402A can correspond to the empty volume of 515 mL. As is illustrated, the bounce in the pressure signal magnitude curve 1402A is relatively small as the curve is substantially flat. The bounce of the pressure signal can be measured using a variety of techniques, such as by measuring peak-to-trough change and selecting the largest such change as being indicative of the largest bounce. Curve 1402A can correspond to the voltage reading, current reading, etc.

FIG. 14B illustrates a magnitude curve 1402B of the pressure signal in the flow path as sensed by one or more pressure sensors over a period of time. Curve 1402B can correspond to a signal observed when the canister and/or one or more dressings are relatively full. For example, the canister may be configured to hold up to 750 mL volume, and curve 1402B can correspond to the empty volume of 60 mL. As is illustrated, the bounce in the pressure signal magnitude curve 1402B is larger than that in curve 1402A. FIG. 14C illustrates a magnitude curve 1402C of the pressure signal in the flow path as sensed by one or more pressure sensors over a period of time. Curve 1402C can correspond to a signal observed when the canister and/or one or more dressings are almost full. For example, the canister may be configured to hold up to 750 mL volume, and curve 1402C can correspond to the empty volume of 30 mL. As is illustrated, the bounce in the pressure signal magnitude curve 1402B is larger than that in curves 1402A and 1402B.

FIG. 14D illustrates a magnitude curve 1402D of the pressure signal in the flow path as sensed by one or more pressure sensors over a period of time. Curve 1402D can correspond to a signal observed when the canister and/or one or more dressings are nearly full. For example, the canister may be configured to hold up to 750 mL volume, and curve 1402D can correspond to the empty volume of 15 mL. As is illustrated, the bounce in the pressure signal magnitude curve 1402D is larger than that in curves 1402A, 1402B, and 1402C.

Table 2 illustrates the largest magnitude bounces or peak-to-trough changes (for example, in voltage as indicated by Vp-p) measured for the curves 1402A, 1402B, 1402C, and 1402D according to some embodiments. With reference to the first row (row 1), column A corresponds to curve 1402A and indicates the largest change of 0.010 V, column B corresponds to curve 1402D and indicates the largest change of 0.078 V, column C corresponds to curve 1402C and indicates the largest change of 0.122 V, and column D corresponds to curve 1402D and indicates the largest change of 0.170 V. These increasing bounce values confirm that the bounce in the pressure signal magnitude increases as the canister fills up or a blockage develops. Level of exudate in the canister (or the one or more dressings) can be detected by comparing the determined pressure magnitude bounce to one or more thresholds, which can be determined experimentally for canisters or dressings of various sizes as described herein. For example, canister (or one or more dressings) pre-full condition may be set to the canister having 30 mL or less empty volume. Using Table 1, a pre-full threshold can be set to approximately 0.12 V peak-to-trough bounce. In some embodiments, measures other than or in addition to peak-to-trough can be used, such as average bounce, etc.

TABLE 2

| Pressure Magnitude Bounce at 40 mmHg | | | | |
|---|---|---|---|---|
| Pressure Magnitude ($V_{p-p}$) at 40 mmHg | D 15 mL volume | C 30 mL volume | B 60 mL volume | A 515 mL volume |
| 1  60 mL/min | 0.170 | 0.122 | 0.078 | 0.010 |
| 2  150 mL/min | 0.174 | 0.120 | 0.074 | 0.012 |
| 3  450 mL/min | 0.178 | 0.118 | 0.068 | 0.008 |
| 4  1000 mL/min | 0.124 | 0.082 | 0.050 | 0.012 |

In some embodiments, signal processing techniques can be utilized on the detected pressure signal(s). For example, sensed pressure values can be processed, such as low-pass filtered (for example, via averaging), to remove noise. As another example, detected pressure signal can be converted into frequency domain, for example by using the Fast Fourier Transform (FFT). The signal can be processed and analyzed in frequency domain.

As is illustrated in FIGS. 14A-14D, the bounce or ripple in the observed pressure magnitude increases as the canister or one or more dressings fill up, which reduces the volume "seen" by the pump. As explained herein, because larger dressings have larger volume "seen" by the pump, the larger dressings can cause smaller peak-to-peak measurements than smaller dressings. By detecting sizes of one or more dressings, the pump system can adopt accurate blockage detection threshold values for different dressing sizes.

Disclosed embodiments of blockage detection can be used in a TNP system that operates substantially without an external leak or external flow of gas (such as, atmospheric air) into one or more fluid flow paths. For example, disclosed embodiments of blockage detection can be used with a Pico TNP system available from Smith & Nephew operating with single or multiple dressings.

Leak Detection

A TNP system can perform leak detection similarly to blockage detection described herein. For example, leak detection can be performed during initial pump down (such as, in the IPD state 1014 of FIG. 10) or in maintenance mode (such as, in the maintenance mode states 1050 of FIG. 10).

FIG. 15 illustrates pressure versus time graphs when a leak condition is detected according to some embodiments. A TNP system or pump assembly (via one or more processors as described herein) can perform leak check test, which may result in detection of a leak or low vacuum. If at any point during a time period that follows initiation of therapy, such as 45 seconds or any other suitable duration after therapy has been started, the pump system transitions from the initial pump down state, such as the IPD state 1014, to a monitoring state, such as the maintenance mode states 1050, the leak check test has passed and suitable seal is deemed to have been achieved. That is, if pressure at the wound has reached desired negative pressure setpoint 1602 within the period of time, it is determined that the one or more fluid flow paths are suitably sealed and no significant leaks are present (for example, the one or more dressings have been properly placed and proper connections between one or more of pump assembly, canister, or dressing(s) have been made).

The pump system can detect a leak condition from the peak-to-trough measurements similarly to performing blockage detection as described herein. With reference to FIG. 15, a pressure profile 1604 of a suitably sealed pump system reaches the pressure setpoint 1602. Once the pressure setpoint 1602 is reached, subsequent pressure measurements may oscillate, as the pressure profile 1602 illustrates, about the pressure setpoint as described herein.

When there exists a leak in one or more fluid flow paths, the pressure profile can follow a leak pressure profile 1606. As illustrated in FIG. 15, the leak pressure profile 1606 does not reach the pressure setpoint 1602. Additionally, the profile 1606 may show peak-to-trough variations 1608 that have relatively small magnitudes (for example, as compared to the blockage peak-to-trough variations in region 1306 of FIG. 13). Still, comparing peak-to-trough measurements 1608 against suitable one or more thresholds, such as the threshold 1612 can ignore variations 1610 from suitably sealed pump systems, but detect small variations 1608 from leaking pump systems, existence of a leak condition can be performed.

In some cases, after leak check test has passed, a suitable seal can be deemed to have been achieved until therapy is paused. After therapy is restarted, leak check test can be performed.

Additional embodiments of blockage or leak detection are described in U.S. Pat. No. 8,843,327, U.S. Patent Publication No. 2016/0184496, International Patent Publication Nos. WO 2016/103033, WO 2016/103035, WO 2016/103032, and WO 2016/103031, and International Application No. PCT/EP2018/056494 (published as WO 2018/167199), each of which is incorporated herein by reference in its entirety.

Terminology

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems or computing devices. Likewise, the data repositories shown can represent physical or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

The invention claimed is:

1. A negative pressure wound therapy apparatus comprising:
    a negative pressure source configured to couple, via a plurality of fluid flow paths, to a plurality of wound dressings and provide negative pressure to the plurality of wound dressings, the plurality of fluid flow paths comprising:
        a first fluid flow path configured to fluidically connect a first wound dressing to the negative pressure source, the first wound dressing with a first fluid retention capacity; and
        a second fluid flow path configured to fluidically connect a second wound dressing to the negative pressure source, the second wound dressing with a second fluid retention capacity;
    at least one pressure sensor configured to measure pressure associated with the plurality of fluid flow paths; and
    a controller configured to operate the negative pressure source, the controller further configured to:
        receive a plurality of pressure measurements from the at least one pressure sensor;
        determine from at least some of the plurality of pressure measurements first and second fluid retention capacities of the first and second wound dressings;
        determine a blockage threshold based at least in part on the determined first and second fluid retention capacities;
        detect presence of a blockage in at least one of the first or second fluid flow paths based at least in part on comparing at least some of the pressure measurements associated with flow of fluid in at least one of the first or second fluid flow paths to the blockage threshold; and
        provide an indication of the blockage in response to determining that the blockage threshold is satisfied.

2. The apparatus of claim 1, wherein the blockage indicates that at least one of the first or second wound dressings contains an amount of fluid that is greater than a capacity threshold but less than the first or second fluid retention capacity.

3. The apparatus of claim 1, wherein the controller is further configured to determine the first and second fluid retention capacities of the first and second wound dressings based on a duration of time for achieving a negative pressure setpoint following activation of the negative pressure source.

4. The apparatus of claim 3, wherein the controller is further configured to deactivate the negative pressure source when the negative pressure setpoint has been achieved.

5. The apparatus of any of claim 3, wherein the duration of time is inversely proportional to a combined first and second fluid retention capacities of the first and second wound dressing.

6. The apparatus of any of claim 1, wherein the controller is further configured to detect a combined first and second fluid retention capacities of the first and second wound dressing.

7. The apparatus of claim 1, wherein the controller is further configured to:
    determine a rate of pressure change in the first and second fluid flow paths based on at least some of the pressure measurements; and
    determine the first and second fluid retention capacities of the first and second wound dressings based on the rate of pressure change.

8. The apparatus of claim 7, wherein the rate of pressure change is inversely proportional to dressing capacity.

9. The apparatus of claim 1, wherein the controller is configured to determine at least one peak-to-trough pressure measurement and detect presence of the blockage based on comparing the at least one peak-to-trough pressure measurement to the blockage threshold.

10. The apparatus of claim 1, wherein the controller is further configured to:
    determine a leak threshold based at least in part on the determined first and second fluid retention capacities;
    detect presence of a leak in at least one of the first or second fluid flow paths based at least in part on comparing at least some of the pressure measurements associated with flow of fluid in at least one of the first or second fluid flow paths to the leak threshold; and
    provide an indication of the leak in response to determining that the leak threshold is satisfied.

11. A method of operating a negative pressure wound therapy apparatus comprising:

by a controller of the negative pressure wound therapy apparatus, operating a negative pressure source of the negative pressure wound therapy apparatus, wherein the negative pressure source is configured to couple, via a plurality of fluid flow paths, to a plurality of wound dressings, the plurality of fluid flow paths comprising:
  a first fluid flow path configured to fluidically connect a first wound dressing to the negative pressure source, the first wound dressing with a first fluid retention capacity; and
  a second fluid flow path configured to fluidically connect a second wound dressing to the negative pressure source, the second wound dressing with a second fluid retention capacity; and
by the controller:
  receiving a plurality of pressure measurements from at least one pressure sensor of the negative pressure wound therapy apparatus;
  determining from at least some of the plurality of pressure measurements first and second fluid retention capacities of the first and second wound dressings;
  determining a blockage threshold based at least in part on the determined first and second fluid retention capacities;
  detecting presence of a blockage in at least one of the first or second fluid flow paths based at least in part on comparing at least some of the pressure measurements associated with flow of fluid in at least one of the first or second fluid flow paths to the blockage threshold; and
  providing an indication of the blockage in response to determining that the blockage threshold is satisfied.

12. The method of claim 11, wherein the blockage indicates that at least one of the first or second wound dressings contains an amount of fluid that is greater than a capacity threshold but less than the first or second fluid retention capacity.

13. The method of claim 11, further comprising, by the controller, determining the first and second fluid retention capacities of the first and second wound dressings based on a duration of time for achieving a negative pressure setpoint following activation of the negative pressure source.

14. The method of claim 13, further comprising, by the controller, deactivating the negative pressure source when the negative pressure setpoint has been achieved.

15. The method of claim 13, wherein the duration of time is inversely proportional to a combined first and second fluid retention capacities of the first and second wound dressing.

16. The method of claim 11, further comprising, by the controller, detecting a combined first and second fluid retention capacities of the first and second wound dressing.

17. The method of claim 11, further comprising, by the controller:
  determining a rate of pressure change in the first and second fluid flow paths based on at least some of the pressure measurements; and
  determining the first and second fluid retention capacities of the first and second wound dressings based on the rate of pressure change.

18. The method of claim 17, wherein the rate of pressure change is inversely proportional to dressing capacity.

19. The method of claim 11, further comprising, by the controller, determining at least one peak-to-trough pressure measurement and detect presence of the blockage based on comparing the at least one peak-to-trough pressure measurement to the blockage threshold.

20. The method of claim 11, further comprising, by the controller:
  determining a leak threshold based at least in part on the determined first and second fluid retention capacities;
  detecting presence of a leak in at least one of the first or second fluid flow paths based at least in part on comparing at least some of the pressure measurements associated with flow of fluid in at least one of the first or second fluid flow paths to the leak threshold; and
  providing an indication of the leak in response to determining that the leak threshold is satisfied.

* * * * *

UNITED STATES PATENT AND TRADEMARK OFFICE
CERTIFICATE OF CORRECTION

PATENT NO. : 11,975,134 B2
APPLICATION NO. : 17/270398
DATED : May 7, 2024
INVENTOR(S) : Felix Clarence Quintanar Page 1 of 1

It is certified that error appears in the above-identified patent and that said Letters Patent is hereby corrected as shown below:

In the Specification

Column 15, Line 56, delete "5108." and insert -- 510B. --.

Column 23, Line 57, delete "Versapore™" and insert -- Versapor™ --.

Column 28, Line 13, delete "in in" and insert -- in --.

Column 42, Line 37, delete "the a" and insert -- the --.

In the Claims

Column 48, Line 32, Claim 5, delete "of any of" and insert -- of --.

Column 48, Line 36, Claim 6, delete "of any of" and insert -- of --.

Signed and Sealed this
Twenty-third Day of July, 2024

Katherine Kelly Vidal
*Director of the United States Patent and Trademark Office*